(12) United States Patent
Silberbach et al.

(10) Patent No.: US 11,464,639 B2
(45) Date of Patent: Oct. 11, 2022

(54) METHODS FOR CREATING SINUS-MATCHED AORTIC VALVES

(71) Applicants: Gary Michael Silberbach, Portland, OR (US); Ming-Chen Hsu, Ames, IA (US); Xiao-Yue Han, Portland, OR (US)

(72) Inventors: Gary Michael Silberbach, Portland, OR (US); Ming-Chen Hsu, Ames, IA (US); Xiao-Yue Han, Portland, OR (US)

(73) Assignees: Oregon Health & Science University, Portland, OR (US); Iowa State University Research Foundation, Ames, IA (US)

(*) Notice: Subject to any disclaimer, the term of this patent is extended or adjusted under 35 U.S.C. 154(b) by 529 days.

(21) Appl. No.: 16/264,634

(22) Filed: Jan. 31, 2019

(65) Prior Publication Data
US 2019/0240025 A1 Aug. 8, 2019

Related U.S. Application Data

(60) Provisional application No. 62/624,790, filed on Jan. 31, 2018.

(51) Int. Cl.
*A61F 2/24* (2006.01)
*A61L 27/36* (2006.01)
(Continued)

(52) U.S. Cl.
CPC ............ *A61F 2/2496* (2013.01); *A61B 34/10* (2016.02); *A61F 2/2409* (2013.01); *A61F 2/2415* (2013.01); *A61L 27/16* (2013.01); *A61L 27/18* (2013.01); *A61L 27/3625* (2013.01); *A61L 27/507* (2013.01); *A61B 2034/105* (2016.02); *A61B 2090/367* (2016.02);
(Continued)

(58) Field of Classification Search
CPC ........ A61F 2/24; A61F 2/2415; A61F 2/2418; A61F 2/2412; A61F 2/2496
See application file for complete search history.

(56) References Cited

U.S. PATENT DOCUMENTS

| 5,156,621 A | 10/1992 | Navia et al. |
| 6,338,740 B1 | 1/2002 | Carpentier |

(Continued)

OTHER PUBLICATIONS

Nistri et al., Aortic root dilatation in young men with normally functioning bicuspid aortic valves, Heart 1999; 82: 19-22.
(Continued)

*Primary Examiner* — Jason-Dennis N Stewart

(57) ABSTRACT

Methods for generating aortic heart valve leaflets are disclosed wherein the aortic sinus surfaces (the inner surfaces of the sinuses of Valsalva) are used as a template to generate geometric representations of replacement aortic heart valve leaflets. As such, sinus-matched replacement leaflets can be sized and shaped according to the patient-specific geometry of the aortic root. Patient-specific aortic valve assemblies based on aortic root and sinus geometry are also described. Methods for estimating the coaptation area of a sinus-matched valve and assessing whether the valve is functionally competent for implantation are described.

10 Claims, 22 Drawing Sheets
(19 of 22 Drawing Sheet(s) Filed in Color)

(51) Int. Cl.
*A61B 34/10* (2016.01)
*A61L 27/50* (2006.01)
*A61L 27/16* (2006.01)
*A61L 27/18* (2006.01)
*A61B 90/00* (2016.01)

(52) U.S. Cl.
CPC ... *A61F 2240/002* (2013.01); *A61F 2240/005* (2013.01); *A61L 2430/20* (2013.01)

(56) References Cited

U.S. PATENT DOCUMENTS

| | | |
|---|---|---|
| 6,585,766 B1 | 7/2003 | Huynh et al. |
| 7,179,290 B2 | 2/2007 | Cao |
| 2003/0163194 A1* | 8/2003 | Quijano ............... A61F 2/2412 623/2.11 |
| 2016/0000560 A1 | 1/2016 | Rankin et al. |

OTHER PUBLICATIONS

Svensson et al., Results of matching valve and root repair to aortic valve and root pathology, The Journal of Thoracic and Cardiovascular Surgery, vol. 142, No. 6, 1491-1498, Dec. 2011.

Vukicevic et al., Experimental study of an asymmetric heart valve prototype, European Journal of Mechanics B/Fluids 35 (2012) 54-60.

* cited by examiner

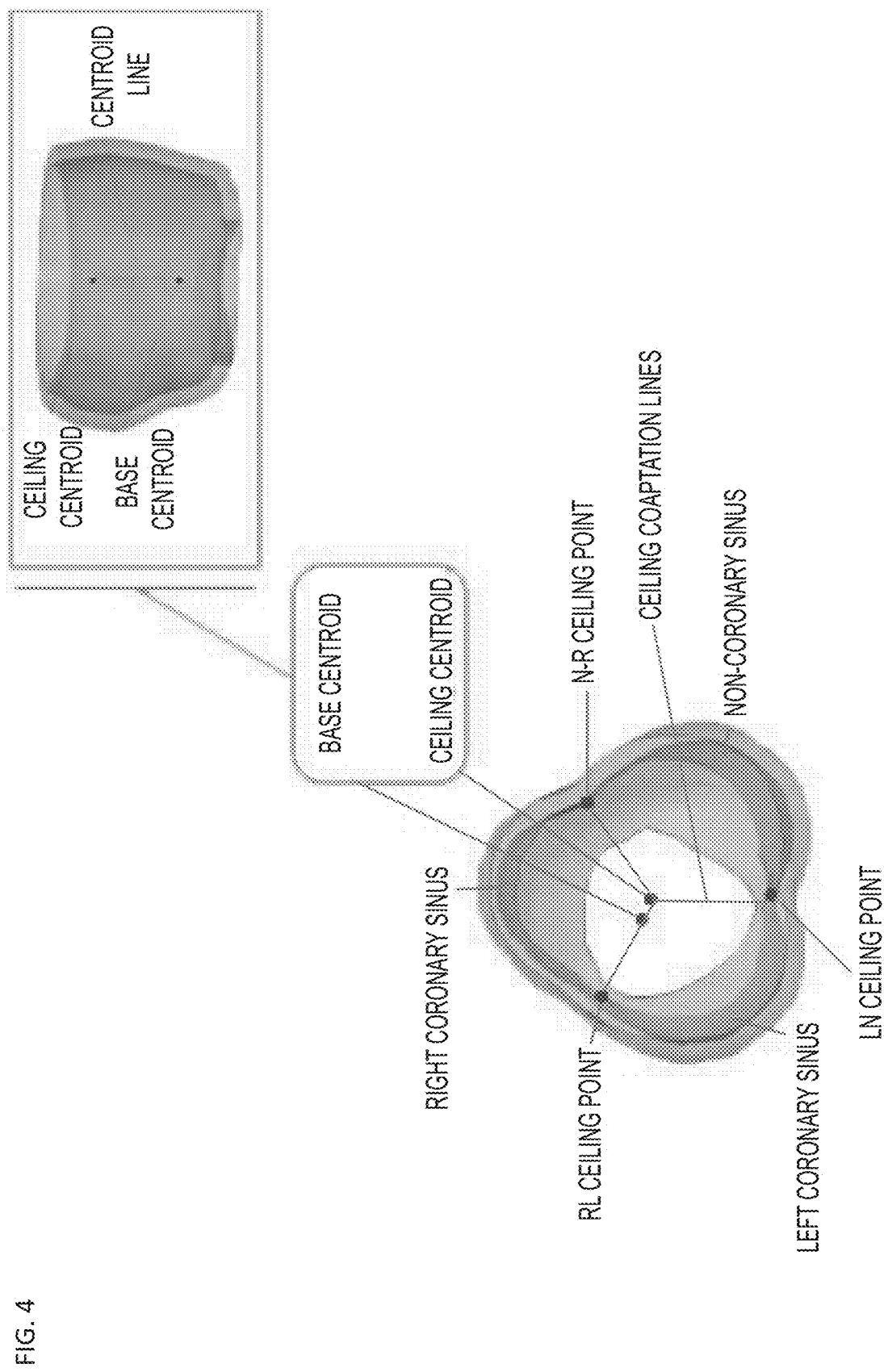

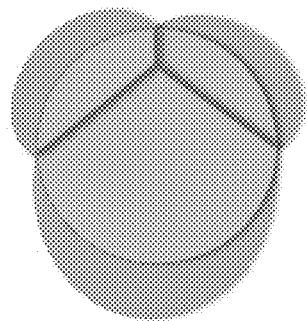
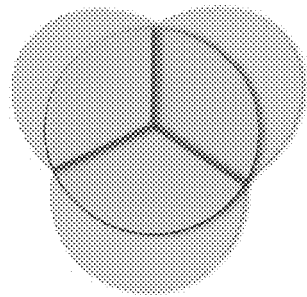
FIG. 10B

METHODS FOR CREATING SINUS-MATCHED AORTIC VALVES

FIELD

Generally, the field is heart valve prostheses. More specifically, systems and methods are presented for generating anatomically correct aortic heart valve leaflet geometries for use in heart valve devices and heart valve repair.

BACKGROUND

Congenitally malformed aortic valves affect 3 million people in the US and nearly 75 million people around the world. Bicuspid aortic valve (BAV), for example, is the most common congenital heart malformation and often leads to aortic stenosis and/or insufficiency. In aortic stenosis the valve thickens and calcifies over time, compromising its ability to open and close fully. This compromised valve function decreases blood flow from the heart and increases the mechanical stress load to which the myocardium is subjected. Consequently, aortic stenosis of the valve can lead to premature aging of the myocardium as pathologic remodeling causes the heart muscle tissue to become thick and stiff in response to the elevated stress load. Operative repair or replacement of the stenotic valve is often required.

The prosthetic heart valves used to replace damaged or diseased heart valves generally fall into two categories: mechanical valves and tissue valves. Mechanical heart valves are robust and have low mechanical failure rates, but their use requires long-term treatment with anticoagulants. Mechanical valves can also produce an audible sound as the rigid valve mechanism opens and closes with each beat of the heart. Tissue valves, by contrast, are flexible, silent, and do not require the use of blood thinners. The most common tissue valves are constructed with whole porcine (pig) valves, or with separate leaflets cut from bovine (cow) pericardium. However, tissue valves are less durable than mechanical valves and can harden (calcify) over time, and can potentially tear under the stresses of continuous operation. Still, tissue valves are increasingly adopted for longer term implantation and as durability and hemodynamic performance improves, their use is expected to grow.

Typically, tissue-type prosthetic valves are constructed by sewing the flexible tissue leaflets onto a supporting rigid frame or stent. These frame or stent structures generally constructed from a metal alloy and have a biocompatible cloth covering to which the leaflets attach. Most frame and stent designs have a circular shaped supporting base with alternating post-like "pillar" structures so that leaflets may be attached in a conformation that mimics the anchoring arrangement of native leaflets. The cloth-covered base frame serves as a suturing ring for attachment of the prosthesis to the wall of the aorta and this is typically the only structural connection of the prosthesis to the patient; the post-like pillars to which the leaflets are attached are not themselves attached to the aorta. While some prosthetic valve designs have moved in the direction of noncircular or asymmetric frames that better conform to the anatomic shape into which they are to be implanted, less attention has been focused on leaflet geometry. This anatomic mismatch of frame and leaflet design is particularly acute for aortic valve repair, where the aortic root has a unique and often asymmetrical sinus morphology within which the valve resides. This sinus morphology is presumed to affect aortic valve function, hemodynamics, and tissue homeostasis. It is therefore of interest to improve prosthetic valve and leaflet design for aortic heart valve applications to account for patient-specific variations in sinus morphology.

SUMMARY

Methods for generating aortic heart valve leaflets and aortic valves are disclosed wherein the aortic sinus surfaces (the inner surfaces of the sinuses of Valsalva) are used as a template to generate geometric representations of replacement aortic heart valve leaflets. As such, sinus-matched replacement leaflets can be sized and shaped according to the patient-specific geometry of the aortic root.

Provided is a method of preparing a template for use in the preparation of an aortic valve leaflet for transplantation into a subject, the method comprising the steps of:
a) receiving three-dimensional anatomical imaging data spanning at least a portion of the aortic root of the subject, the portion of the aortic root having a proximal end and a distal end, an inner aortic root surface, and an aortic sinus surface;
b) identifying a first and second ceiling point and a base point for the aortic sinus surface;
c) identifying a third ceiling point on the an inner aortic root surface;
d) truncating the aortic sinus surface at the level of a plane passing through the first, second, and third ceiling points, thereby generating a truncated aortic sinus surface;
e) calculating a second plane passing through the first and second ceiling points and the base point of the truncated aortic sinus surface;
f) calculating an intersection of the second plane and the aortic sinus wall surface, thereby defining a sinus-matched leaflet surface; and
g) forming a template having dimensions corresponding to the sinus-matched leaflet surface.

Also provided is an aortic valve leaflet prepared by the steps of:
a) receiving three-dimensional anatomical imaging data spanning at least a portion of the aortic root of the subject, the portion of aortic root having a proximal end and a distal end, an inner aortic root surface, and an aortic sinus surface;
b) identifying a first and second ceiling point and a base point for the aortic sinus surface;
c) identifying a third ceiling point on the an inner aortic root surface;
d) truncating the aortic sinus surface at the level of a plane passing through the first, second, and third ceiling points, thereby generating a truncated aortic sinus surface;
e) calculating a second plane passing through the first and second ceiling points and the base point of the truncated aortic sinus surface;
f) calculating an intersection of the second plane and the aortic sinus wall surface, thereby defining a sinus-matched leaflet surface;
g) forming a template having dimensions corresponding to the sinus-matched leaflet surface; and
h) preparing an aortic valve leaflet corresponding to the template.

Also provided is a stentless aortic valve prosthesis prepared by the steps of:
a) receiving three-dimensional anatomical imaging data spanning at least a portion of the aortic root of the subject, the portion of the aortic root having a proximal end and a distal end, an inner aortic root surface, and three aortic sinus surfaces;

b) identifying a first, second, and third ceiling point on the an inner aortic root surface;

c) identifying a third ceiling point on the an inner aortic root surface;

d) truncating the aortic sinus surface at the level of a plane passing through the first, second, and third ceiling points, thereby generating a truncated aortic sinus surface;

e) for each of the three aortic sinus surfaces:

f) identifying a first and second ceiling point and a base point for the aortic sinus surface;

g) calculating a construction plane passing through the two ceiling points and the base point of the truncated aortic sinus surface;

h) calculating an intersection of the plane and the truncated aortic sinus surface to define a concave leaflet surface;

i) extracting from the concave leaflet surface a leaflet wall curve where the concave leaflet surface is in contact with the construction plane;

j) constructing an anchoring flange surface based on the leaflet wall curves from each of the three aortic sinus surfaces; and k) joining the three concave leaflet surfaces with the anchoring flange to form a stentless aortic valve prosthesis.

Methods are also provided for incorporating a suture ring based on patient-specific sinus shape into the stentless aortic valve prosthesis.

Also described are methods for estimating the coaptation area of sinus-matched aortic valve that has been created using the disclosed methods and assessing whether the valve is functionally competent for implantation.

It is an object of the invention to produce valve leaflets that are tailored to an individual's native sinus anatomy and are competent in diastole, such that the area of coaptation is sufficient to ensure that blood does not flow back through the valve when it is in a closed position.

It is an object of the invention to create a replacement aortic valve based on a subject's native sinus geometry such that, when the diseased stenotic valve is replaced, the total coaptation area of sinus-matched replacement valve falls in the same range of total coaptation areas seen for sinus-matched valves generated from a normal, non-stenotic aortic root.

It is an object of the invention to produce valve leaflets that promote normal coronary blood flow.

It is an object of the invention to generate a replacement valve that conforms to patient-specific anatomy such that the impedance of the blood flow profile is minimized when the valve is in the open (systolic) position.

It is an object of the disclosed methods to create valve leaflet geometries matched to sinus morphology such that the blood flow regimen in the sinus space is improved compared to off-the-shelf prosthetic aortic valves. By better recapitulating normal hemodynamics in the sinus-cusp complex over a cardiac cycle, a valve fitted with sinus-matched leaflets is designed to improve coronary blood flow, and engender a more natural flow-induced shear stress and fluid structure interaction regime at the leaflet and sinus surfaces.

This Summary is provided to introduce a selection of concepts in a simplified form that are further described below in the Detailed Description. This Summary is not intended to identify key features or essential features of the disclosed subject matter, nor is it intended to be used to limit the scope of the disclosed subject matter. Furthermore, the disclosed subject matter is not limited to implementations that solve any or all disadvantages noted in any part of this disclosure.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Embodiments will be readily understood by the following detailed description in conjunction with the accompanying drawings. Embodiments are illustrated by way of example and not by way of limitation in the figures of the accompanying drawings.

FIG. 4 shows a reference geometry of an aortic root structure used for generating sinus-matched leaflet geometries and calculating coaptation area.

FIG. 10B shows a schematic representation of relationship between predicted coaptation areas and sinuses for normal, symmetric valves (control) and diseased, asymmetric valves (case).

DETAILED DESCRIPTION

Figure 1:
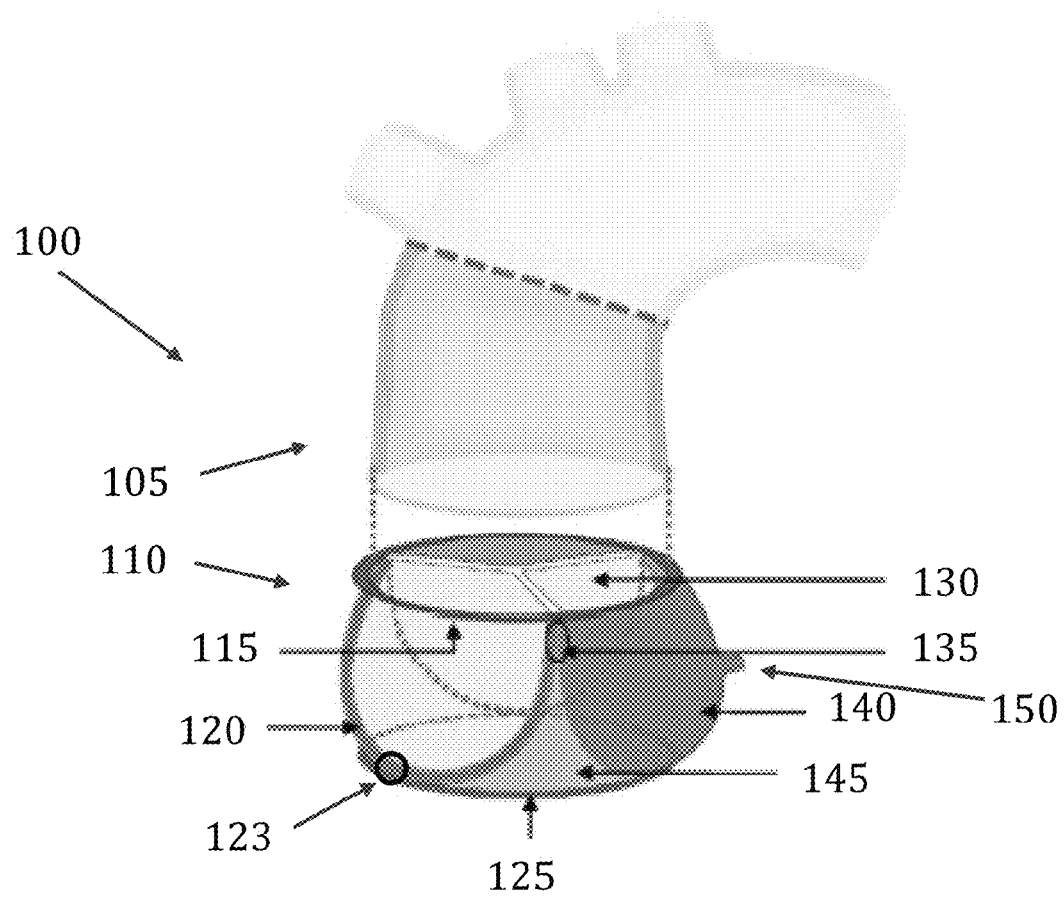
FIG. 1 shows a schematic drawing depicting the anatomy of an aorta and aortic heart valve.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the present invention, the phrase "A/B" means A or B. For the purposes of the present invention, the phrase "A and/or B" means "(A), (B), or (A and B)". For the purposes of the present invention, the phrase "at least one of A, B, and C" means "(A), (B), (C), (A and B), (A and C), (B and C), or (A, B and C)". For the purposes of the present invention, the phrase "(A)B" means "(B) or (AB)" that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

Embodiments herein provide methods for creating patient-specific aortic heart valve leaflet replacements for use in prosthetic aortic valve applications. As disclosed herein, aortic leaflet geometries are derived from the patient-specific morphology of the aortic sinuses, and as such, reflect inherent asymmetry of the patient's own anatomy. Also disclosed are methods to allow for the creation of a personalized aortic valve prosthesis with leaflets that coapt in a manner that ensures competency during the diastolic phase of blood flow. Embodiments are also provided for incorporating an optional suturing ring into a personalized heart valve assembly, wherein the suturing ring is configured to conform to the patient-specific anatomy to enhance device stability without unduly deforming or otherwise stressing the natural cross sectional shape of the aortic root and annulus or interrupting the flow profile during the cardiac cycle or compromising coronary blood flow.

It is understood that the methods, aortic valves, leaflets, prosthetics, and other aspects described herein are included for use in mammalian patients or subjects. In some embodiments, they are included for use in human patients or subjects. In some embodiments they are intended for use in infants, children, adolescents, and adults.

In some embodiments, the aortic valve prosthesis described above is a bioprosthesis. In some embodiments, the bioprosthesis comprises porcine tissue. In other embodiments, the bioprosthesis comprises bovine tissue. In still other embodiments, the bioprosthesis comprises human tissue.

FIG. 1 shows a schematic view of the relevant anatomical structures comprising the aorta 100 as used in this disclosure. The term "aortic root" 110 as used herein refers to the section of the aorta 100 closest to and attached to the heart, consisting of the aortic valve leaflets (or cusps) 130, the sinuses of Valsalva 140, the leaflet attachments 120, the interleaflet triangles (or "pillars") 145, the sinotubular junction 115, the ventriculo-aortic junction 125, and openings for the coronary arteries 150. During the systolic phase of the cardiac cycle, blood is pumped from the left ventricle, entering the proximal side of the aortic root 110 at the ventriculo-aortic junction 125, passing through the open leaflets 130 of the aortic valve, and exiting the distal aortic root 110 at the sinutubular junction 115 and onward to the ascending aorta 105. The terms "leaflet" and "cusp" 130 refer to the semilunar sheet of material that may comprise one of the three hinged valve surfaces or flaps opened and closed during the cardiac cycle. As used herein, both leaflet and cusp may also refer to those aspects of a natural cardiac valve or manmade or natural materials cut, modeled, molded, or otherwise manufactured or prepared to serve as a replacement leaflet or cusp for transplantation purposes, either alone or as part of a framework comprising three leaflets oriented and secured to function as a cardiac tricuspid valve. The term "nadir points" 123 refers to the anatomic points at which the three aortic valve leaflets 130 connect proximally to the wall of the left ventricular outflow tract at the hinge point of each aortic leaflet. When identified in tomographic images these nadir points 123 are also referred to as "base points" for purposes of leaflet reconstruction. The terms "Sinuses of Valsalva" 140 or "aortic sinuses" refers to the anatomic dilations of the ascending aorta just above the ventriculo-aortic junction 125. The term "sinotubular junction" 115 refers to the well-defined ridge at the top of a sinus, marking the point of transition from the aortic root to the ascending aorta. Reference to a "commissure point" 135 herein refers to the anatomic point where two 130 valve leaflets come together at the distal 110 aortic root and are attached to the aortic wall. When identified in tomographic images these points are also referred to as "ceiling points" for purposes of leaflet reconstruction. The aortic annulus refers to the fibrous ring at the proximal base of the aortic root 110, and comprises a virtual basal ring at the level of the ventriculo-aortic junction 125 passing through the nadir points of each of the aortic leaflets 130. The term "aortic surgical annulus" 120 refers to the three-dimensional fibrous crown-shaped structure that circumscribes the aortic root 100, passing through the cusp nadir points 123 proximally and the commissure points distally 135, and is the site of insertion of the aortic valve leaflets 130 along the sinus wall.

The terms "bioprosthesis" and "bioprosthetic" as used herein refers to a prosthetic device comprising an animal part or an animal tissue, including porcine, bovine, or human parts or tissues. In particular, they refer to sheets of natural tissue used to form any portion of a prosthetic device, including a framework or leaflets (cusps) for cardiac valve repair or replacement.

The terms "imaging" or "medical imaging" or "anatomical imaging" herein refer to techniques and process used to create visual representations, either in the form of two-dimensional image data (images) or three-dimensional image data (image stacks), of the interior of a subject's body for clinical analysis, diagnosis, or medical treatment. Examples of medical imaging useful for the present uses include Magnetic Resonance Imaging (MRI), cardiac MRI, computed tomography (CT)-angiography, or three-dimensional echocardiography.

During a cardiac cycle blood flow from the left ventricle to the aorta passes through the semilunar aortic valve, normally comprising three cusps or leaflets, though a percentage of the population congenitally has only two cusps or leaflets. Normally, there are three anatomic dilations occurring just above the aortic valve: (a) the left posterior aortic sinus, which gives rise to the left coronary artery; (b) the anterior aortic sinus, which gives rise to the right coronary artery; and (c) the right posterior aortic sinus, also referred to as the non-coronary sinus. These sinuses may be collectively referred to as the sinuses of Valsava.

In optimum conditions, the three aortic sinuses have substantially the same sizes and shapes, with the three similarly-shaped valve leaflets meeting at or near their collective midpoint from three ceiling points, as seen in the "Control" orientation in FIG. 10B. In some individuals, though, the sinuses are of different arrangements, such as depicted in the "Case" example of FIG. 10B, giving rise to dissimilar leaflets that meet at a point other than the midpoint. In some individuals, three sinuses are present, but the valve is congenitally comprised of only two leaflets or cusps, forming a bicuspid aortic valve. In a very small subset of individuals with bicuspid aortic valve, only two sinuses are discernible. However in the majority of individuals with a bicuspid aortic valve three sinuses are present. For example in a study described below, among 50 individuals with known bicuspid aortic valve all but two cases had 3 sinuses present.

Conventional prosthetic heart valves are typically arranged in a uniform manner of the Control image in FIG. 10B. The present methods, devices, and materials described herein are intended to create valve or leaflet replacements in alignment with an individual's specific and unique aortic sinus morphology so that non-uniform or asymmetric sinus anatomy is accommodated.

Described herein are methods for preparation of a personalized aortic valve leaflet using tomographic image data that encompasses the aortic root of a subject. Also provided are methods directed to the preparation of a personalized aortic valve comprising three leaflets and an anchoring flange to allow said personalized aortic valve to be attached to the wall of the aortic root. A further embodiment of a personalized aortic valve is also described wherein an anatomically shaped and sized suturing ring is incorporated into the anchoring flange assembly at a variable level along the surgical aortic annulus.

In the stenotic aortic heart valve, the leaflets often become progressively malformed as scarring and calcification lead to thickening and stiffening of the leaflet. This stenosis of the leaflets impedes their normal motion during systole and diastole, decreasing the normal blood flow from the heart during ejection. Consequently, increased pressure in the left ventricle leads to premature aging of the myocardium as pathologic remodeling causes the heart muscle tissue to become thick and stiff in response to the elevated stress load. Restoration of aortic valve function by repair or replacement of the valve leaflets is therefore an important mode of treatment for myocardial disease.

Figure 2:
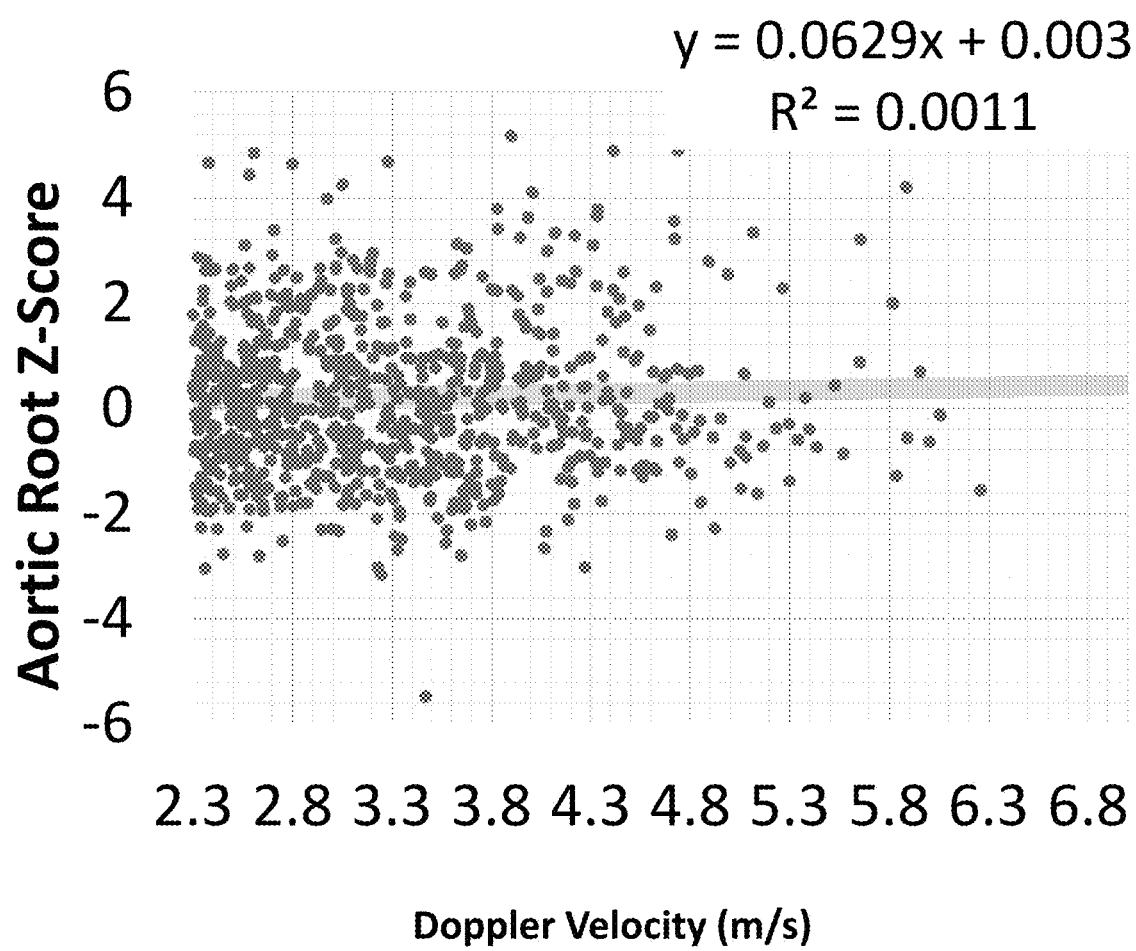
FIG. 2 is a plot of aortic root z-score as a function of aortic stenosis severity as estimated by Doppler velocity measurement.

Previous work has shown that the severity of aortic stenosis has a very limited relationship to aortic root diameter (Nistri S, et al, "Aortic root dilatation in young men with normally functioning bicuspid aortic valves", *Heart* 82, 19-22 (1999); incorporated by reference herein). A review of echo data comparing Doppler velocity (an indicator of stenosis severity) and aortic root diameter demonstrates no correlation between the two parameters (FIG. 2). It has also been suggested that for normal valve function, there is a critical relationship between each valve leaflet and its corresponding sinus (Svensson, L. G. et al, "Results of matching valve and root repair to aortic valve and root pathology," *The Journal of Thoracic and Cardiovascular Surgery* 142:6, 1491-1498, (2011); incorporated by reference herein). The left and right coronary sinuses are the origination sites of blood flow into the left and right coronary arteries, respectively, and therefore the hemodynamics of the cusp-sinus region play an important role supplying blood to the myocardium. In addition, it has been shown that vortex formation between a sinus and its corresponding valve cusp plays a role in valve closure, and may also produce a scouring shear stress to prevent formation of thrombi behind the cusps (Bellhouse B J and Bellhouse F H, "Mechanism of closure of the aortic valve," *Nature* 217, 86-7 (1968), incorporated by reference herein).

The healthy mammalian aortic valve occupies two extreme positions during a cardiac cycle, closed and open. In the closed position (diastole) the three cusps of the aortic valve flatten as they lean against one another to form a "Mercedes Benz logo"-like shape of a circle divided equally into thirds from its center point—this configuration is termed "coaptation." When the aortic valve is fully open the leaflets invert and a substantial portion of the downstream surface of each leaflet comes into contact with the internal wall of its respective aortic sinus. The inventors have observed that the shapes of the leaflets in this opened valve configuration closely resemble the shape of the internal surface of their respective sinuses.

In the setting of a diseased aortic valve, however, the valve leaflets are small, thickened, and deformed. As such, diseased valve leaflets have no resemblance to the aortic sinuses. Nevertheless, the abnormal valve leaflet's respective aortic sinus grows and develops in a normal fashion independently of the stunted growth of its companion valve leaflet. FIG. 2 provides supporting data to suggest that stenotic aortic valve severity does not affect sinus diameter. This suggests that even in the case of a diseased aortic valve, the size and morphology of the internal surface of the sinus can be used as a template to produce a leaflet geometry that would be morphologically equivalent to a leaflet that had grown normally.

Disclosed herein are methods for the creation of replacement heart valve leaflets that are sized and shaped to reflect a patient's own native heart valve anatomy. The methods are based on the observation that when the aortic valve is open (systole), aortic leaflets are substantially congruent to the aortic sinus surfaces (the inner surfaces of the sinuses of Valsalva). Thus, the aortic sinus surfaces can be used as a template to create replacement leaflets which are dimensioned to recapitulate the patient's functional anatomy and ensure that the valve leaflet shape and the aortic sinus are structurally matched.

Figure 3A:
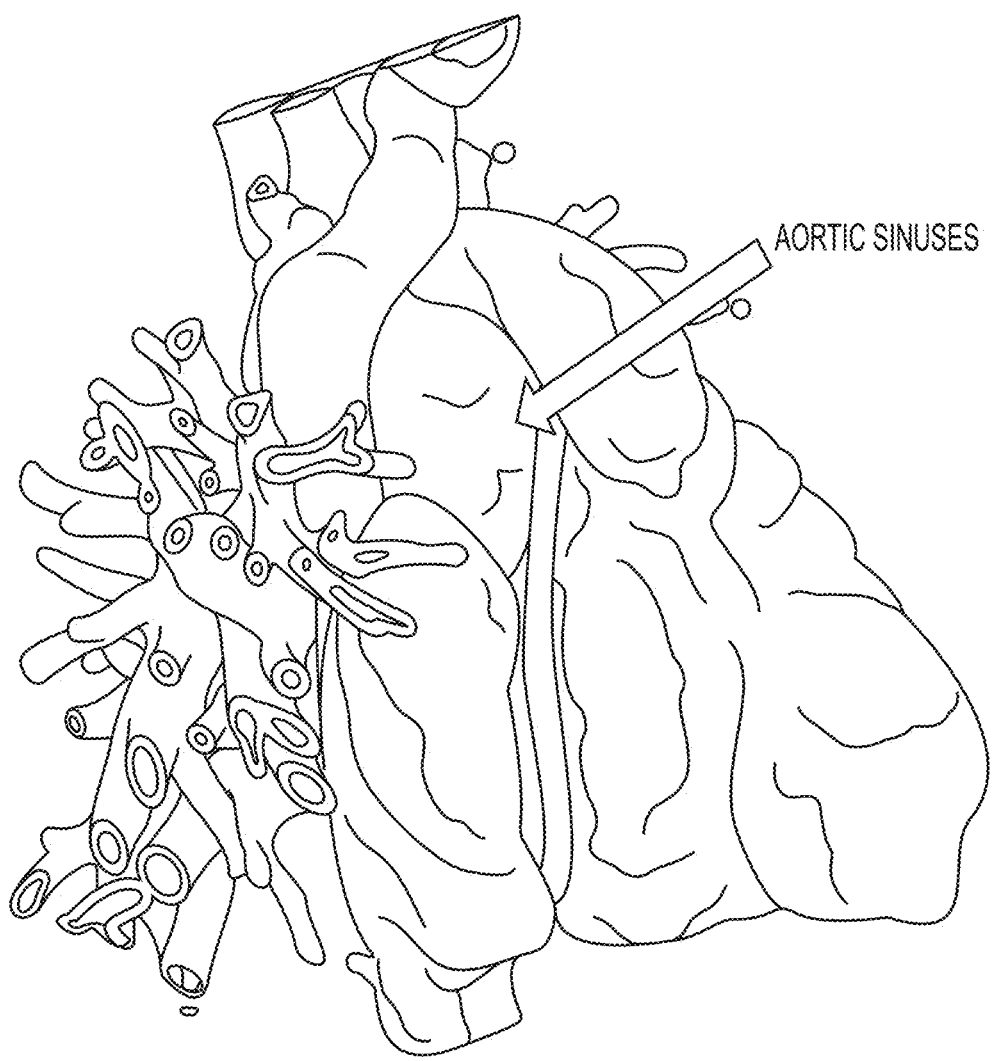
FIG. 3A is a computer rendering of a blood pool image of a heart.

In one embodiment, the method entails receiving three-dimensional anatomic image data spanning the aortic root anatomy. Tomographic imaging techniques such as cardiac Magnetic Resonance Imaging (MRI), computed tomography (CT)-angiography, or three-dimensional echocardiography, for example, can be used to noninvasively provide such image data. FIG. 3A shows an example of a three-dimensional image reconstruction of the blood pool of a human heart obtained by cardiac MR angiography with the location of the aortic sinuses identified.

The anatomic image data are segmented using appropriate image analysis tools known in the art to isolate the aortic root and associated structures. For example, segmented structures can include the aortic root and aortic sinuses within which the leaflets (or cusps) reside, a portion of the ventricles proximal to the root including the three nadir points along the ventriculo-aortic junction, and a distal portion of the aortic root encompassing the three commissures along or near to the sinotubular junction.

Next the inner surface of the aortic root is segmented to provide the geometry of the aortic sinuses from which a replacement leaflet geometry will be defined. In embodiments, the inner surface of the aortic sinuses may be described using representations known in the computer aided geometric design arts for defining surfaces. Examples include parametric representations such as spline, Bezier, b-spline, or NURBS surfaces, or nonparametric surface representations such as triangle tessellations or trimmed surfaces. The inner surface of the aortic sinuses may further be truncated by a passing a plane through the three commissure points and discarding the portion of the surface distal to said plane. A leaflet geometry corresponding to a given sinus may be defined by specifying a bounded portion within the remaining sinus surface to serve as a leaflet surface geometry (corresponding to a concave leaflet configuration in the open or systolic position)., the In a preferred embodiment, the leaflet surface geometry representation may be recovered by intersecting a plane (referred to herein as a construction plane, or an intersection plane) with the inner surface of the aortic sinuses and calculating the curves defining the intersection between said plane and the inner surface of the aortic sinuses. The curves calculated by such an intersection define the bounding edges of a leaflet geometry surface. An intersection plane used for this operation may be defined for each sinus by specifying points through which said plane is constrained to pass. For example, in a preferred embodiment, for a given sinus, two commissure locations (referred to as ceiling points) may be specified at or near to the sinotubular junction where the free ends of the leaflet cusp attaches to the wall of the aorta and one nadir point location specified at the apex of the cusp attachment at the annulus (referred to as a base point). This triple of points may be used to generate a construction plane that is constrained to pass through said three points. Boolean operations may be used to intersect this construction plane with the aortic sinus surface of the segmented aortic root geometry to isolate the relevant portion of the sinus surface of interest, thereby defining a replacement leaflet surface geometry that is matched to its associated sinus.

In some embodiments, a replacement leaflet surface geometry may further be mirrored across its respective construction plane to represent the leaflet in a convex conformation corresponding to a closed or diastolic position. When a plane is used in this manner, it may also be referred to as a mirror plane. Such a mirrored convex leaflet will have continuity along its arcuate lower cusp edge and commissure regions with the wall of the sinus and the free edge of the cusp will extend inward towards the centerline of the aortic root. Representation of leaflets in this mirrored conformation can be advantageous for assessing the coaptation area of leaflets derived from sinus geometry, a method for which is described in greater detail below.

It should also be understood that in some embodiments, leaflet surfaces generated from underlying sinus surface geometry may be further edited by performing operations such as smoothing, scaling, trimming, warping, or augmenting its curved surface into a desired shape. For example, the free edge of a leaflet can be made smaller or the leaflet geometry otherwise modified in order catch the earliest phase of retrograde blood flow (the beginning of diastole) in order to initiate valve closure (see Bellhouse B J and Bellhouse F H, "Mechanism of closure of the aortic valve," Nature 217, 86-7 (1968), incorporated by reference herein).

Figure 3B:
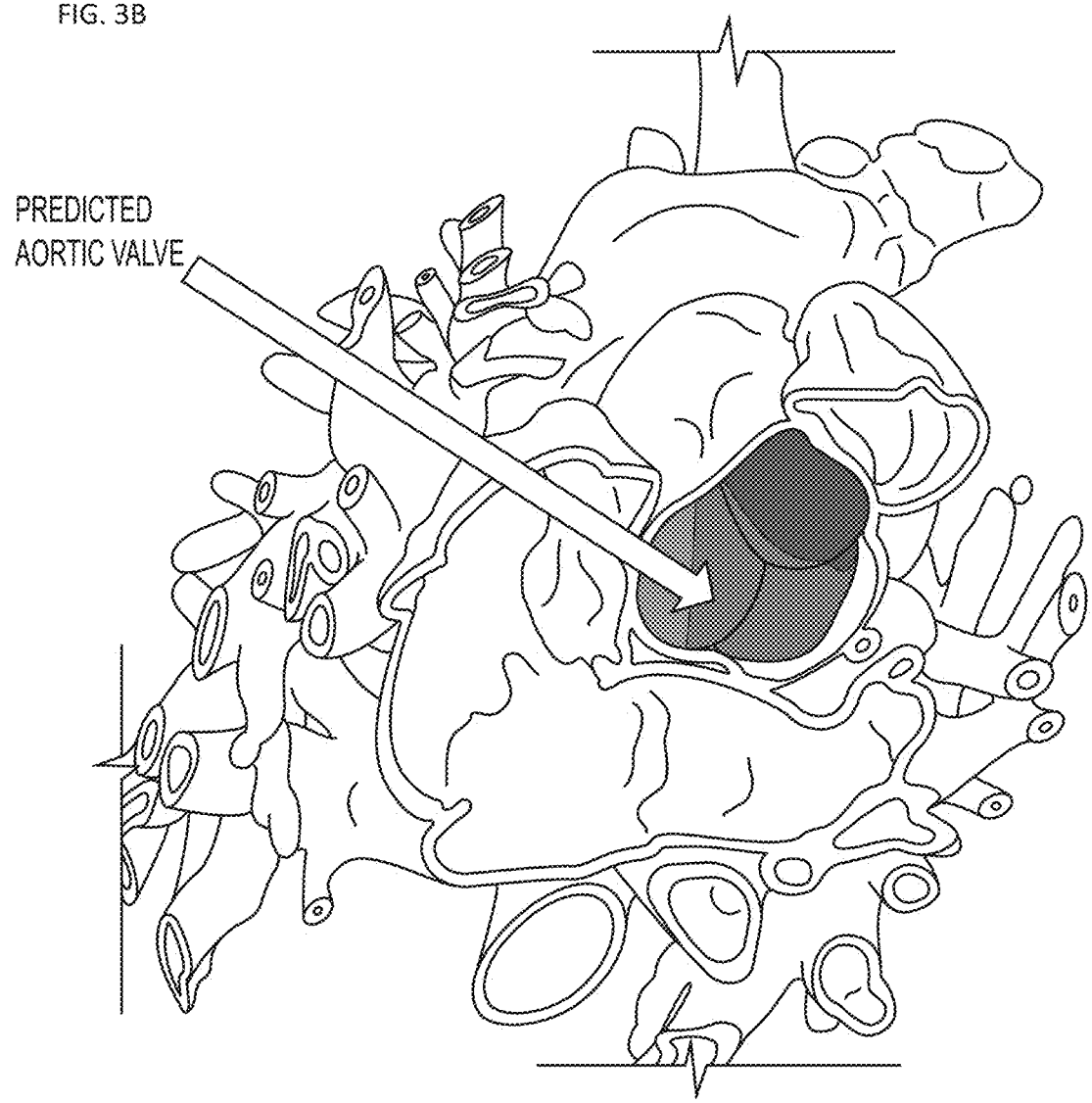
FIG. 3B is a computer rendering showing an aortic valve in situ wherein the leaflets in a diastolic configuration are generated by mirroring a patient's unique aortic sinus shape towards the midline of the aortic root (red, blue=sinus wall surfaces, green=mirrored sinus surfaces to generate a valve in diastolic (i.e., closed) configuration.

FIG. 3B shows a sectioned view of the 3D reconstructed heart of FIG. 3A. The sectioning plane is taken at the approximate level of the proximal aortic root annulus to reveal the interior of the aortic root. A set of three predicted aortic valves (depicted in green) are shown. These predicted valves were generated and mirrored into the diastolic position using the sinus-matching method described above.

In some embodiments, the sinus-based geometry of the leaflet recovered from patient imaging data may be used to generate a template for use in the preparation an aortic valve leaflet for transplantation into a subject. Such a template may be generated using the concave (open, systolic) or convex (closed, diastolic) representation of the leaflet geometry. In some embodiments the template may comprise a solid material formed into a three-dimensional form over which leaflet-forming material may be draped and sized. In other embodiments, the template may be a planar form to which material may be draped or sized. In other embodiments, the template may comprise a geometric representation of the leaflet in digital form, which may be utilized by devices to mechanically size and prepare a leaflet or project guide lines directing the sizing and preparation of the leaflet. In further embodiments, the representation of the leaflet in digital form may be used as input to a 3D printing or additive manufacturing system to generate a replacement leaflet.

It is understood that in some embodiments the template formed from the methods herein would allow for additional material in the leaflet to accommodate adhering the leaflet into position in a heart valve, whether in vivo directly to tissue or in a valve prosthesis. It is also understood that in some embodiments a template may be used to form a leaflet having a smaller surface area to accommodate the dimensions of another material or device with which it is utilized, such as a framework, stent, or other valve replacement device or material.

Figure 5A:
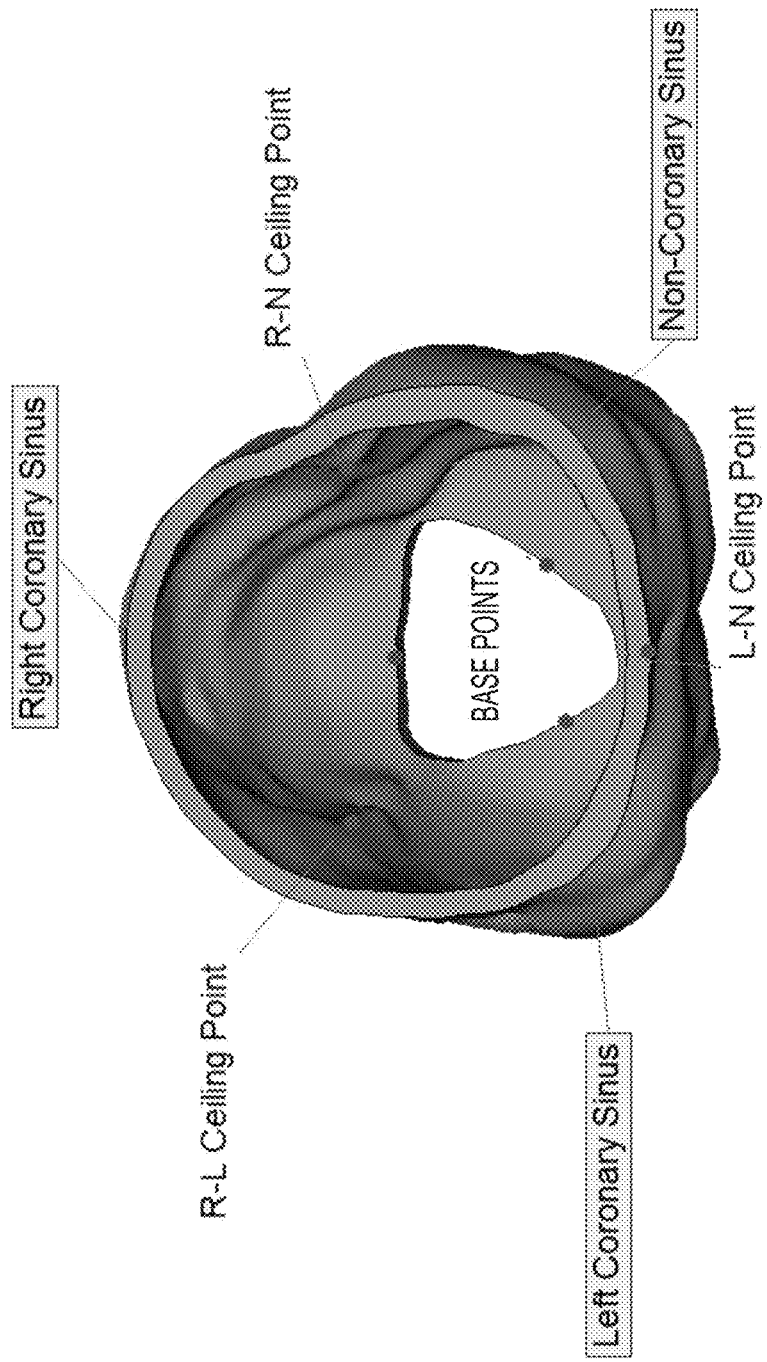
FIG. 5A shows an example of a step in a workflow to generate sinus-matched leaflets. In this step the coordinates of three ceiling points and three base points are identified.

An exemplary workflow for generating sinus-matched leaflet geometries is further demonstrated in FIG. 4 and FIGS. 5A-5G. Turning to FIG. 4, a reference geometry for a segmented aortic root reconstruction is depicted with number of geometric features identified thereon. As shown the aortic root is comprised of three sinuses as follows: the Right Coronary Sinus, Left Coronary Sinus, and Non-Coronary Sinus. The upper boundary of the segmented aortic root, where blood flow is directed outward to the aorta during ventricular systole, is referred to as the "ceiling" end of the structure in this segmented reconstruction, and the lower boundary, where blood flow enters the aortic root from the ventricle during systole, is referred to as the "base" end of the structure. The commissure locations at the ceiling end of the structure are designated as "RL Ceiling Point", "LN Ceiling Point", and "NR Ceiling Point" to identify the commissure points at the junction between the right and left coronary sinuses, the left and non-coronary sinuses, and the non- and right coronary sinuses, respectively. The plane passing through these three ceiling points represents the distal boundary of the replacement valve. The location of a point called "Ceiling Centroid" is calculated using the locations of "RL Ceiling Point", "LN Ceiling Point", "N-R Ceiling Point" along with the three lengths of the free edges of each leaflet generated by the methods described herein. The Ceiling Centroid represents the distal-most point of tri-leaflet coaptation of the replacement valve. A method for calculating the "Ceiling Centroid" location is described below. At the base end of the structure, three "Base Points" (as depicted in FIG. 5A) corresponding the inferior-most attachment location of each cusp to its complementary sinus surface (i.e., the nadir points) are identified. For a given sinus, the two Ceiling Points and Base Point define a construction plane or mirror plane across which the sinus surface may be reflected. The location of a point called the "Base Centroid" is identified as the proximal-most intersection point of the three mirrored leaflets generated using the methods described herein (i.e., the proximal-most point of common coaptation). The axial line segment connecting the Ceiling Centroid and the Base Centroid is designated as the "Centroid Line," and is characterized by a length and an orientation.

Figure 5B:
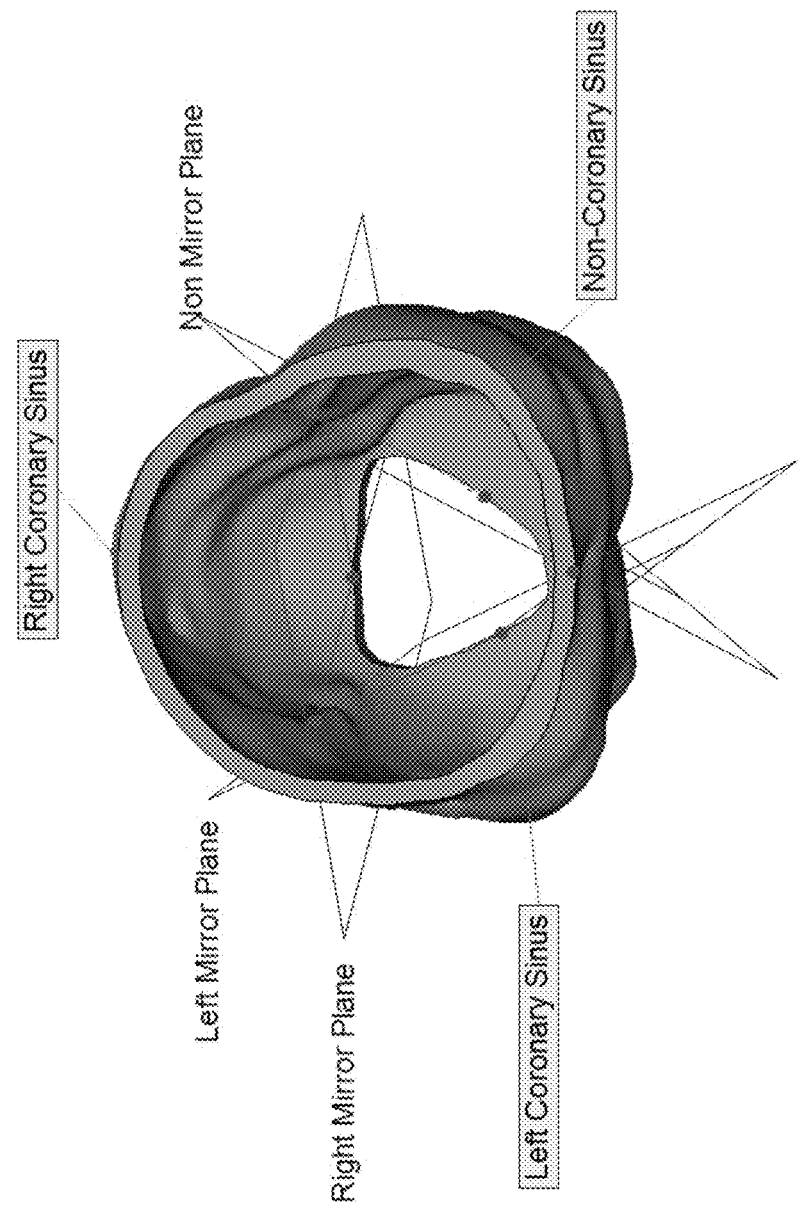
FIG. 5B shows an example of a step in a workflow to generate sinus-matched leaflets. In this step three mirror planes are constructed using the ceiling points and base points.
Figure 5C:
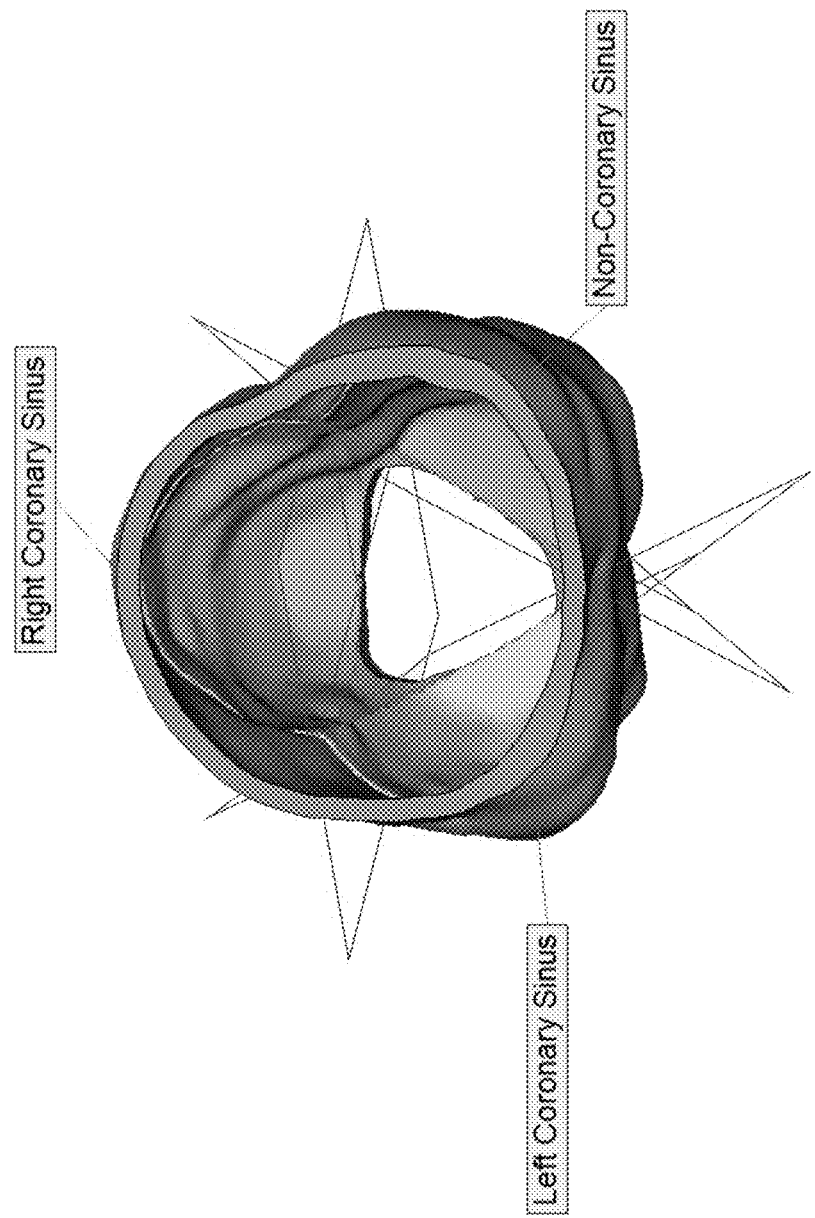
FIG. 5C shows an example of a step in a workflow to generate sinus-matched leaflets. In this step a portion of each sinus surface is selected using the intersection of mirror planes with the aortic root geometry.

FIG. 5A shows a segmented reconstruction of an aortic root structure comprised of a Right Coronary Sinus, Left Coronary Sinus, and Non-Coronary Sinus. The RL, LN, and NR ceiling points are identified along with a set of three base points (the R, L, and B basepoints). FIG. 5B shows the set of three mirror planes constructed from the triples of ceiling and base points, wherein the Right Mirror Plane corresponding to the Right Coronary Sinus is defined using the RL ceiling, NR ceiling, and R basepoints; the Left Mirror Plane corresponding to the Left Coronary Sinus is defined using the LN ceiling, RL ceiling, and L basepoints; and the Non-Mirror Plane corresponding to the Non-Coronary Sinus is defined using the NR ceiling, LN ceiling, and N basepoints. FIG. 5C shows the cusp-shaped surfaces that are recovered from each sinus surface when its mirror plane is intersected with aortic root geometry and appropriate Boolean operators applied. Note that each recovered surface has a concave cusp shape that is congruent with its corresponding sinus wall, but covers less surface area than the full sinus wall.

It will be readily apparent to those with skill in the art that the aforementioned methods may be used to generate a sinus-matched valve leaflet from any of the sinus walls alone or in combination (i.e., one, two, or three leaflets). It will further be appreciated that a set of three sinus-matched valve leaflets generated using the above method may be joined to form a replacement valve structure. Additional description of such a replacement vale embodiment is presented below.

It will further be appreciated that the shapes and dimensions of the sinus matched leaflets recovered by the method described above may be further modified as needed before being assembled into a valve structure. For example, the leaflets may be resized or otherwise modified to ensure that during systole, the leaflet surface does not come into full contact or adhere to the sinus wall surface. The resulting small distance between the superior edge of the leaflet and sinus wall surface produced by resizing the geometry may serve to accommodate valve function at the earliest diastolic phase by catching retrograde blood thereby further expanding the distance between sinus and leaflet and initiating valve closure.

Figure 5D:
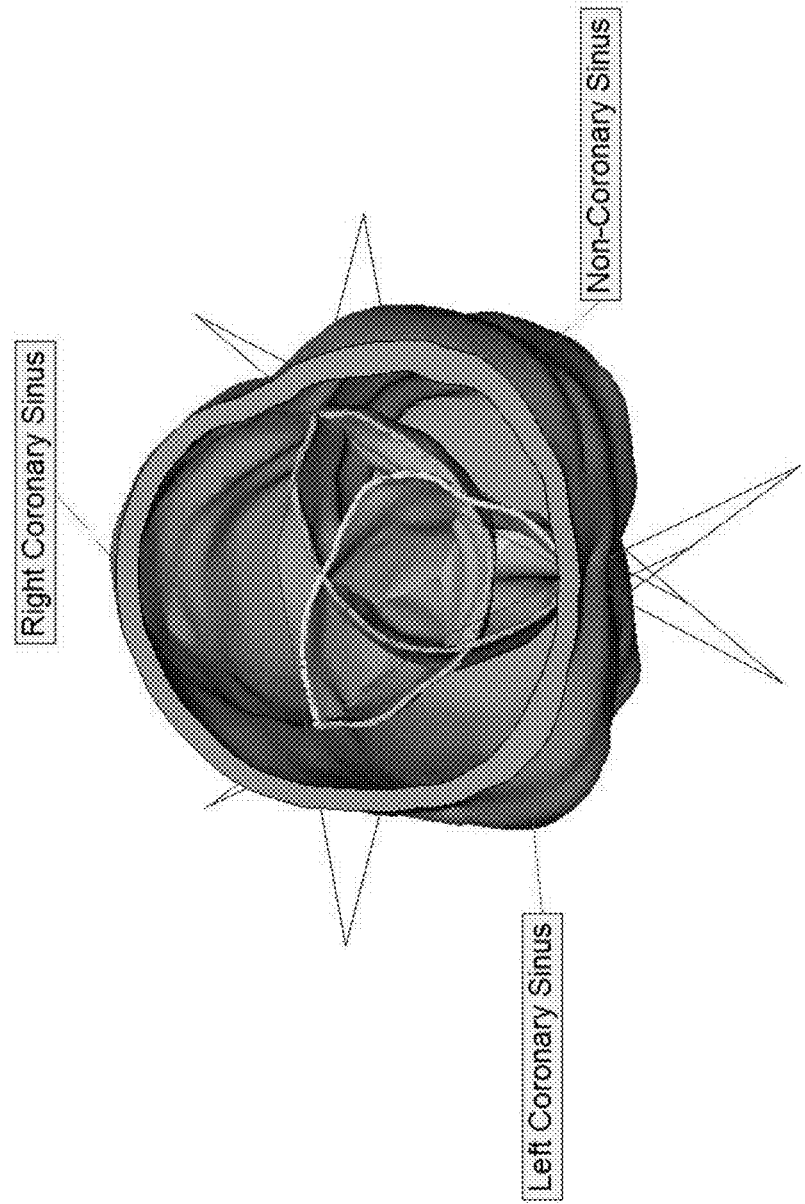
FIG. 5D shows an example of a step in a workflow to measure coaptation area of sinus-matched leaflets. Here, each portion of sinus surface selected in the previous operation is reflected across its corresponding mirror plane.

As noted above, representation of sinus-matched leaflets in a mirrored conformation (i.e., in a convex or diastolic conformation) can be advantageous for assessing the coaptation area of a valve assembled from the leaflets. This assessment is important from a quality control perspective because in order for a valve to function properly, it must close sufficiently that blood will not flow back into the ventricular chamber from which it was just ejected—that is, the valve must be competent. In one aspect, visualization of the three sinus-matched leaflets in the diastolic conformation provides a visual indicator of the degree of overlap between the three valves. FIG. 5D shows the leaflet surfaces produced when the recovered surfaces of FIG. 5C are mirrored across their respective mirror planes (i.e., the Right Mirror Plane, Left Mirror Plane, and Non-Mirror Plane) to produce a set of sinus-matched valve leaflets in convex conformation (the mirror plane in this example is the same plane as the construction plane used to generate the concave leaflet geometry). Note that the mirrored leaflet geometries intersect and overlap centrally within the aortic root, providing visual confirmation that the sinus-matched leaflets should provide some degree of coaptation. However, it is desirable to quantitatively characterize the actual coaptation surfaces that would result from the leaflets leaning against one another during diastole. Such a quantification facilitates the comparison of the coaptation area of a replacement valve generated through sinus-matching to the range of coaptation areas found in a population of normal (healthy), structurally competent valves generated using the same sinus-matching approach.

Figure 5E:
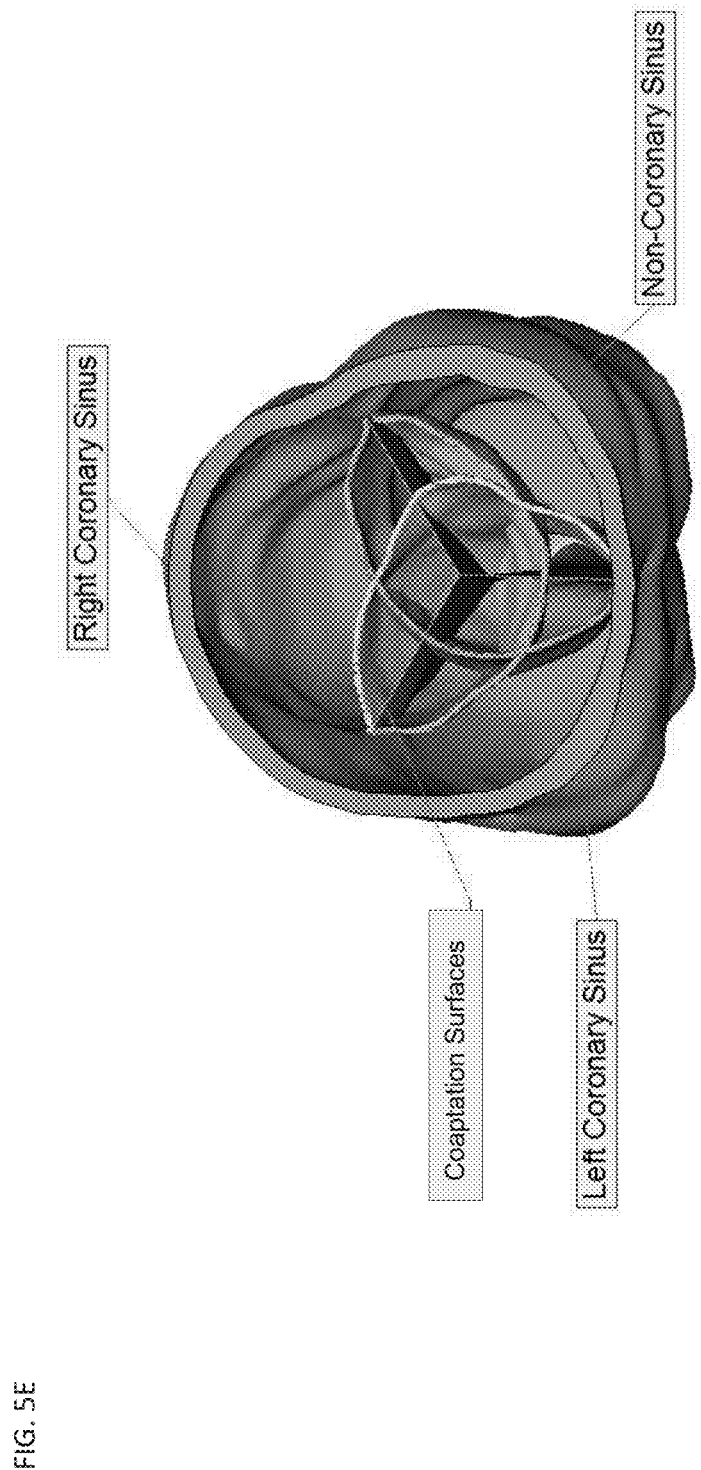
FIG. 5E shows an example of a step in a workflow to measure coaptation area of a set of sinus-matched leaflets. A set of three surfaces are constructed and visualized along with the three sinus-mirrored leaflet geometries.
Figure 5F:
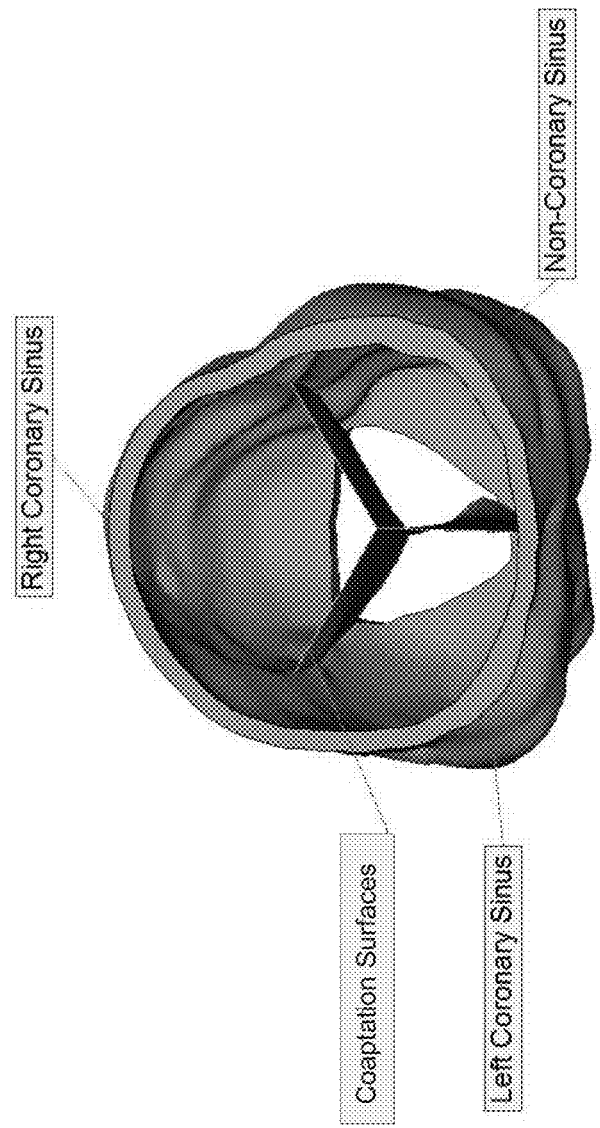
FIG. 5F shows an example of a step in a workflow to measure coaptation area of a set of sinus-matched leaflets. The surfaces depict the coaptation area between the valve leaflets.

Turning to FIG. 5E and FIG. 5F, a set of three Coaptation Planes are constructed to determine valve coaptation area. These planes are used to calculate three separate coaptation area values, each value representing the interactions of an adjacent pair valve leaflet surfaces. Once calculated, the three coaptation areas can be summed to estimate total coaptation area, which can serve as a measure of valve competency. To construct these planes, the coordinates of a Ceiling Centroid are calculated using the two sets of equations along with a compatibility condition to facilitate their solution.

Figure 6:
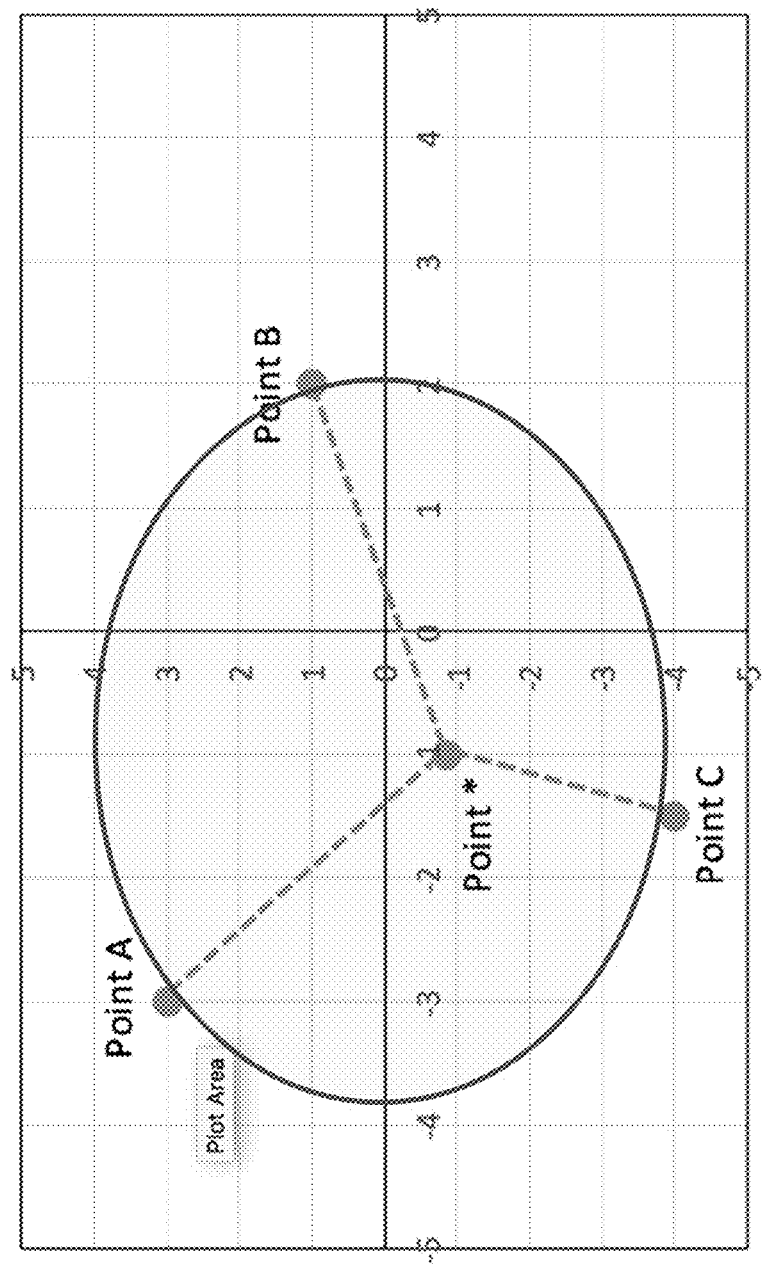
FIG. 6 is a plot depicting the calculation of ceiling centroid coordinates where Points A, B, and C are Ceiling Points, Point * is the Ceiling Centroid, and the lines connecting points A*, B*, and C* represent Ceiling Coaptation lines.

Equation set 1 defines the distance between the Ceiling Centroid point (Point * as depicted in FIG. 6, which is initially unknown) and each leaflet's ceiling point (Points A, B, and C) and the sum of the three lengths ($L_T$). Subscripts denote the x and y components of the position of the points A, B, C, and *.

Equation Set 1

$$\overline{a^*} = \sqrt{(a_x - {^*}_x)^2 + (a_y - {^*}_y)^2} \quad 1.$$

$$\overline{b^*} = \sqrt{(b_x - {^*}_x)^2 + (b_y - {^*}_y)^2} \quad 2.$$

$$\overline{c^*} = \sqrt{(c_x - {^*}_x)^2 + (c_y - {^*}_y)^2} \quad 3.$$

$$\overline{a^*} + \overline{b^*} + \overline{c^*} = L_T \quad 4.$$

Equation Set 2 specifies that the total length of the leaflet free edges ($E_T$) is the sum of the free edge lengths of each leaflet ($E_n$, $E_r$, and $E_l$ for leaflets N, R, and L, respectively). These individual leaflet free edges lengths can be measured from the leaflet geometries generated using the sinus mirroring method described herein.

Equation Set 2

$$E_a + E_b + E_c = E_T \quad 1.$$

Equation Sets 1 and 2 can be solved to calculate the Ceiling Centroid point coordinates by specifying that the proportion of a leaflet's edge length to the sum edge length of all three free edges is equal to the ratio of the lengths between the Ceiling Centroid point and the leaflet's center point to the sum of all three lengths, expressed as follows:

$$\frac{E_a}{E_T} = \frac{\overline{a^*}}{L_T} \quad 1.$$

$$\frac{E_b}{E_T} = \frac{\overline{b^*}}{L_T} \quad 2.$$

$$\frac{E_c}{E_T} = \frac{\overline{c^*}}{L_T} \quad 3.$$

The coordinates of the Base Centroid, as described previously, can be determined by marking the lower-most intersection point of the three mirrored valve leaflets generated using the methods described herein. The Centroid Line can be constructed as the line segment having the Ceiling Centroid and the Base Centroid as endpoints.

Figure 5G:
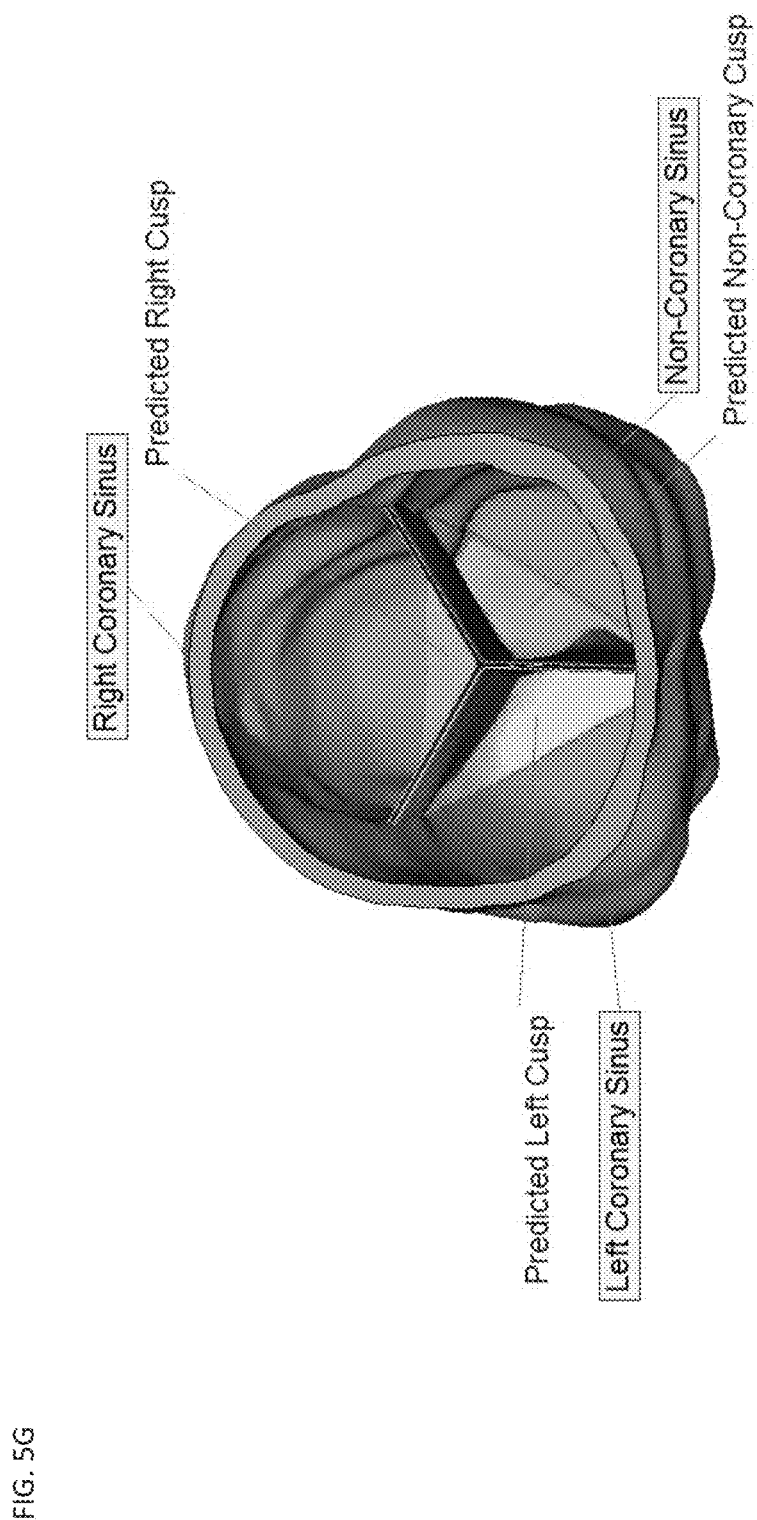
FIG. 5G shows an example of a step in a workflow to measure coaptation area of a set of sinus-matched leaflets. Predicted cusp areas are shown.

Coaptation areas may then be estimated by specifying the boundaries of the closed planar polygons delineating the Coaptation surfaces shown in FIG. 5F and measuring their areas. The Coaptation surface boundaries may be defined superiorly by the respective Ceiling Coaptation Line, medially by the Centroid Line, and inferiorly by the intersection of two overlapping leaflets (FIG. 5E and FIG. 5F). The coaptation areas constructed in this manner also represent an estimate of the conformation of the predicted valves in diastole (FIG. 5G).

The disclosed methods to create a set of three sinus-matched leaflets may also be used to create a patient-specific stentless aortic valve for implantation into the aortic root.

Stentless aortic valves have been designed that take advantage of materials that are sturdy and flexible that can readily be attached to the aortic wall (see for example, U.S. Pat. No. 5,156,621). These materials can be a variety of fabrics or textiles that can be natural substances or chemically created such as Dacron (polyethylene terephthalate). These textiles can be woven threads or printed using, for example, 3D printing or other additive manufacturing techniques. Stentless valves provide advantages over stented bioprosthetic aortic valve designs by improving the flow profile of blood moving through the valve. The resulting lower transvalvular gradients cause favorable remodeling of the left ventricle (i.e., decreased left ventricular muscle mass).

In some embodiments, the present disclosure advances the art of stentless valve design by providing methods that take advantage of the unique geometry of the human aortic sinuses in those with aortic valve disease. It is understood that the shape of the valve can work in concert with the shape of the sinuses to improve the bioprosthesis function. In U.S. Pat. No. 6,342,070 a method is disclosed for implanting cadaver sinuses and valves into a patient, but this approach discards the natural sinuses of the patient. The methods disclosed in present disclosure describe the creation of replacement valve leaflets that match the patent's natural sinuses shapes and do not necessitate removal of the patient's native sinus anatomy. The present disclosure describes novel improvements in the design of stentless valves to facilitate attachment of the sinus-matched valve leaflets to the wall of the patient's natural aortic sinus using an anchoring flange and, optionally, a valve suturing ring, each described below.

Figure 11:
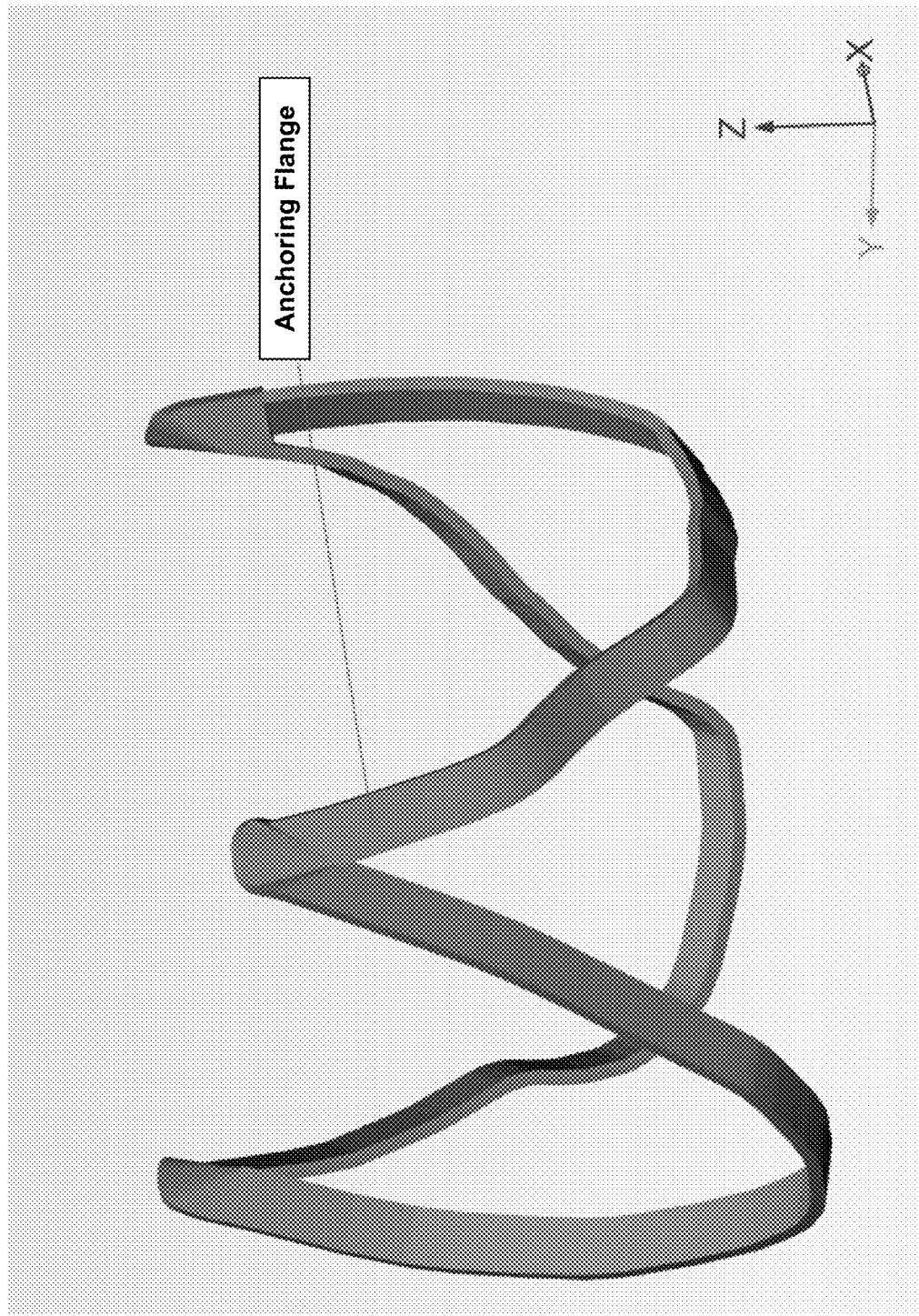
FIG. 11 shows an example of a patient anatomy-based anchoring flange as described herein.

FIG. 11 shows an example of an anatomically derived anchoring flange to which sinus-matched replacement leaflets may be affixed or otherwise manufactured as a single integrated assembly to create a stentless valve construct. Comparing the shape of the anchoring flange in FIG. 11 to the anatomic structures depicted in FIG. 1, it will be appreciated that the centerline of the anchoring flange is substantially aligned with the crown-like shape of the surgical annulus 120. Using the construction plane technique described above for generating sinus matched leaflet geometries, the curves comprising the bounding edges of the sinus matched leaflet at the sinus wall can be defined and used for the generation of a patient-specific anchoring flange. For example, utilizing these leaflet edge curves as a centerline for modeling a thin, narrow tape-like geometry, an anatomically shaped anchoring flange component having a specified width can be created. The width of said anchoring flange is designed to be sufficient to allow suturing to the sinus walls along the entire length of the flange. Exemplary flange widths may range from 0.5 mm to 8 mm and will depend on patient anatomy, mechanical considerations, ease of use, and other factors.

Figure 12:
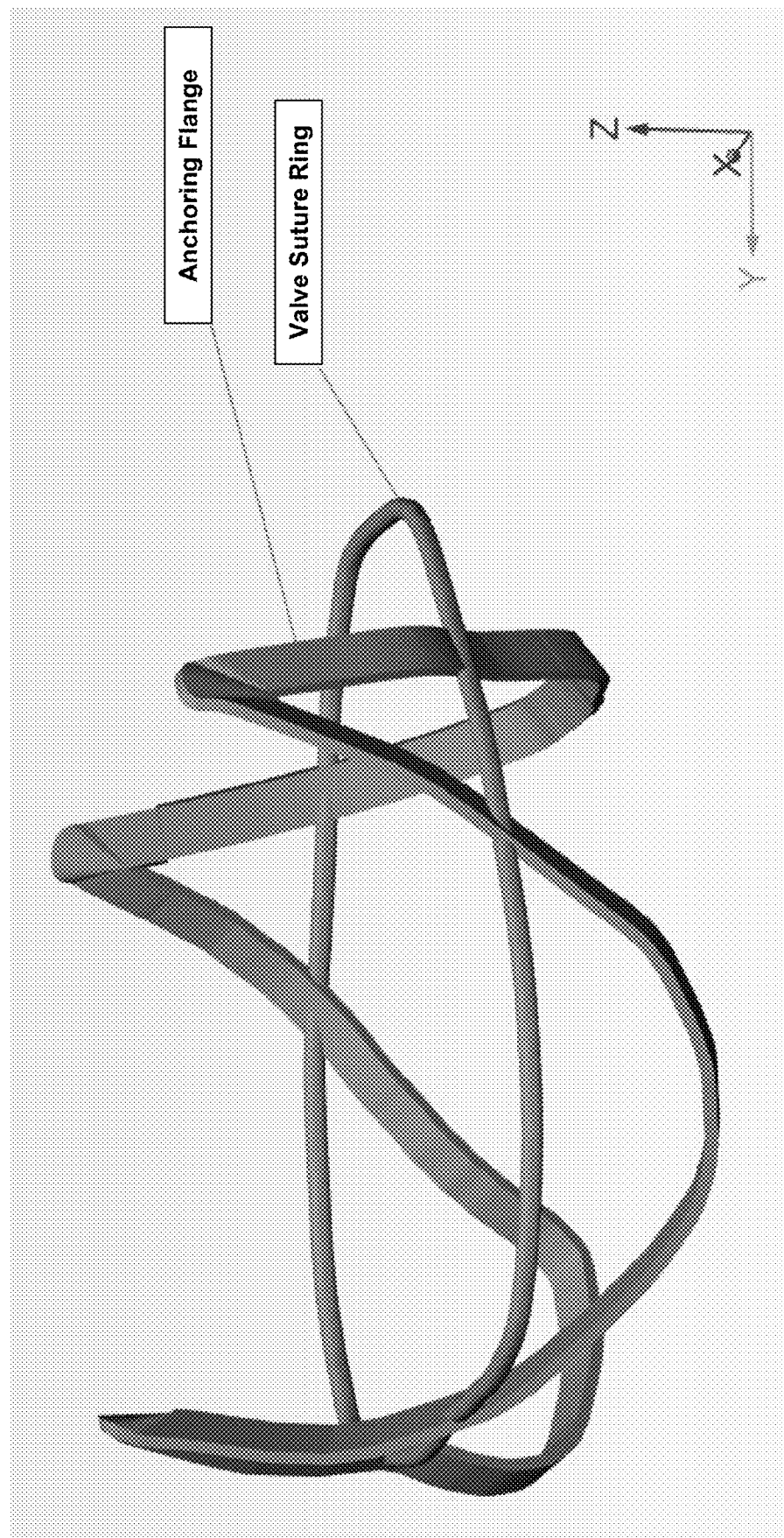
FIG. 12 shows an example of a patient anatomy-based valve suture ring as described herein (same patient as in FIG. 11)

In an alternate embodiment of a patient-specific stentless aortic valve, an optional anatomically shaped valve suture ring can be incorporated into the replacement valve assembly. An example of such a suturing ring, affixed to an anchoring flange, is shown in FIG. 12. The shape of the suturing ring is based on the unique sinus anatomy of the patient as determined using a sectioning plane through the aortic surgical annulus in a manner similar to that used to generate the bounding edge curves of sinus-matched leaflet described earlier. A personalized suturing ring can be generated at different locations along the proximal to distal longitudinal position through the aortic surgical annulus, provided that the position of the ring does not impede coronary blood flow from the right or left coronary sinuses.

In some embodiments, the suturing ring is comprised of a cloth-covered rigid material, for example a biocompatible metal alloy covered by a Dacron fabric. In other embodiments, the suturing ring can be comprised of a flexible material such as a biocompatible polymer or a flexible cord.

Figure 13:
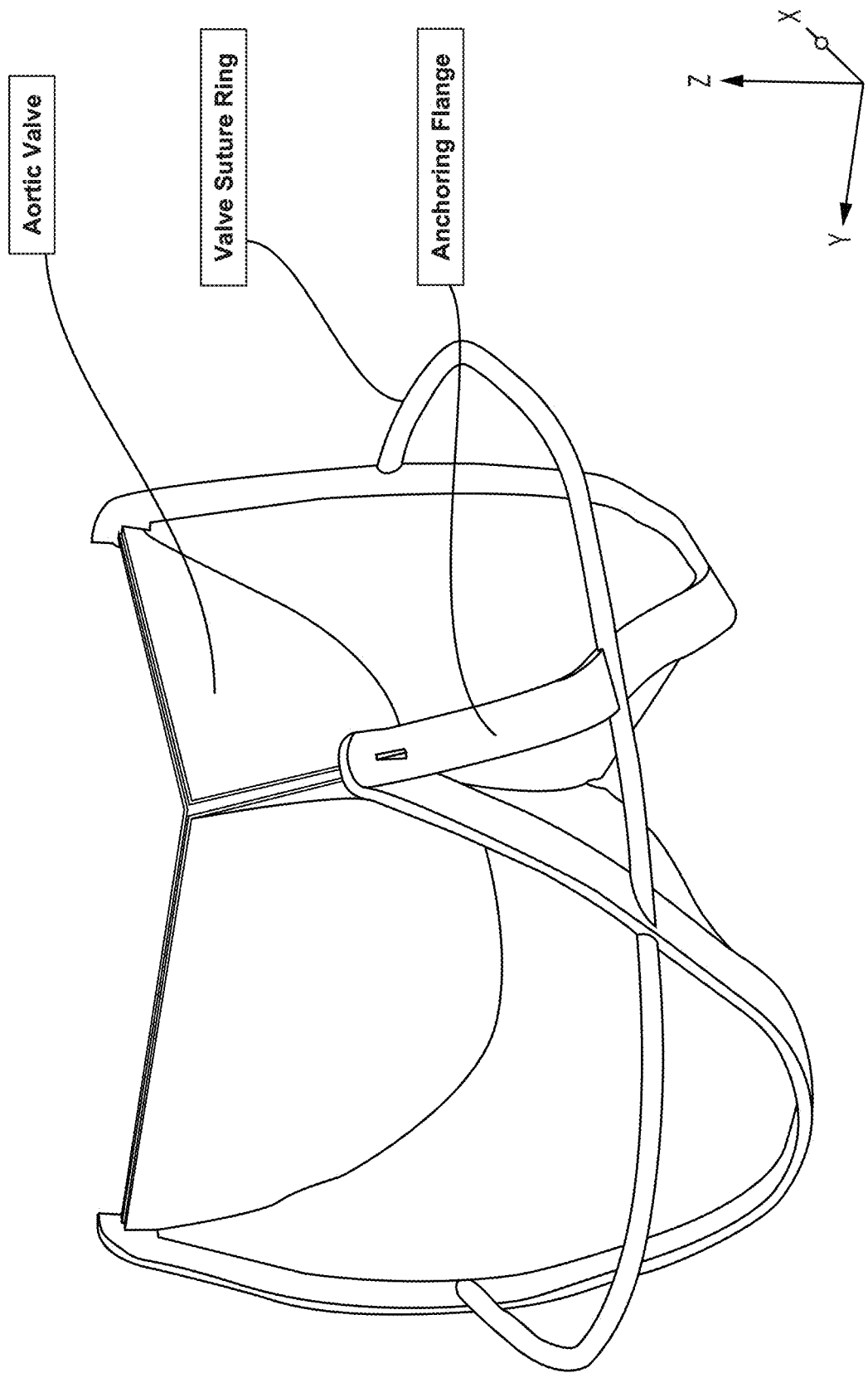
FIG. 13 shows an example of a patient-specific replacement aortic valve comprised of three leaflets, an anchoring flange, and a valve suture ring, generated using the methods described herein (same patient as in FIG. 11).
Figure 14:
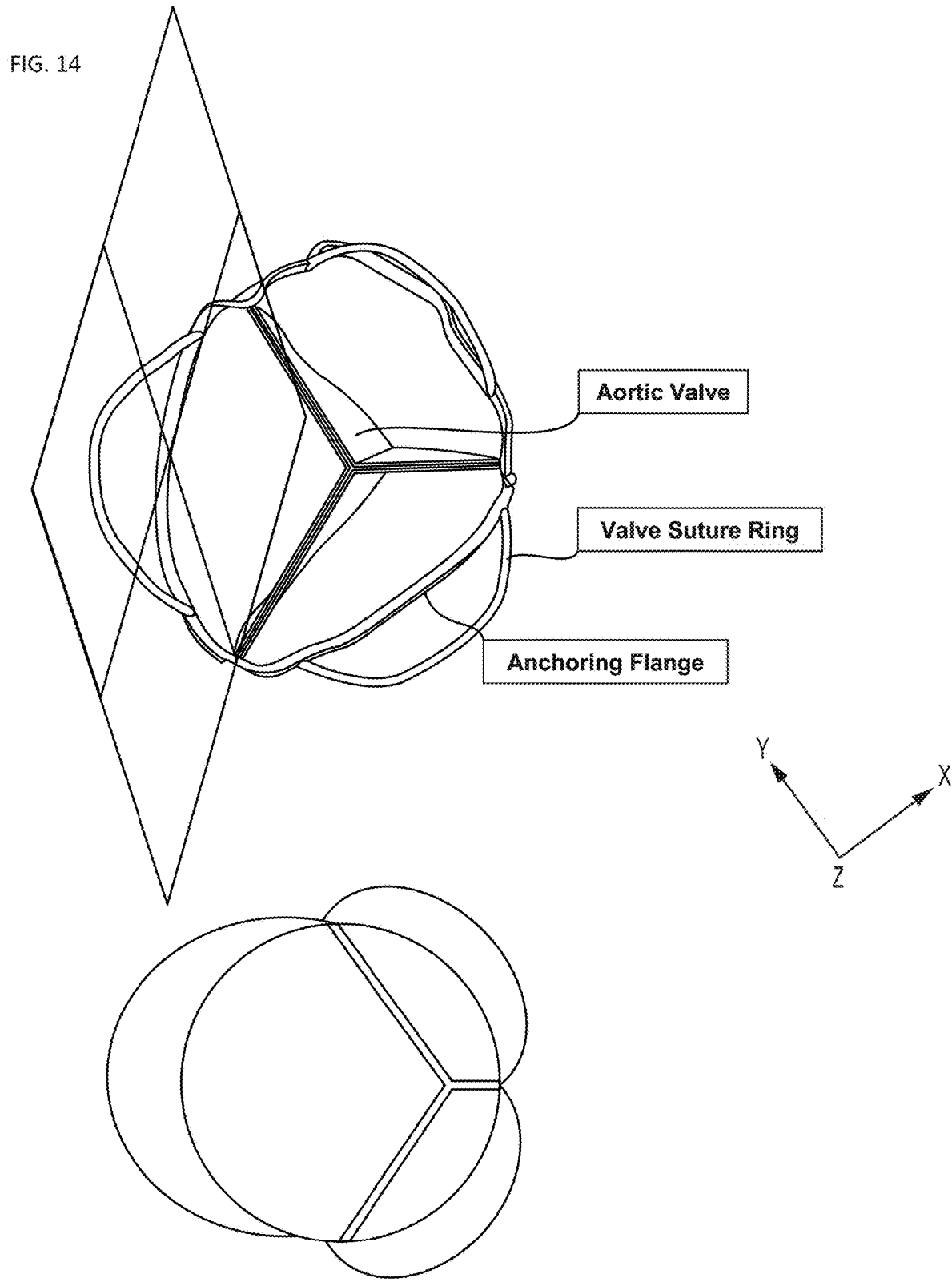
FIG. 14 shows a distal-to-proximal view of a replacement aortic valve comprised of three leaflets, an anchoring flange, and a valve suture ring, generated using the methods described herein from a patient with an asymmetric sinus of Valsalva (same patient as in FIG. 11). An idealized schematic from the same perspective of an asymmetric valve is show for comparison.

FIG. 13 shows an example of a personalized aortic valve assembly having sinus-matched leaflets in the coapted conformation, an anchoring flange affixed to and connecting the valve leaflets, and an anatomically shaped valve suture ring positioned approximately midway between the proximal and distal ends of the aortic root. FIG. 14 shows an example of the personalized aortic valve assembly of FIG. 13 as viewed from the distal to proximal direction. This view highlights the sinus-based anatomic shape of the valve suture ring and the asymmetry of the sinus geometry. This valve was generated from image data from a patient with asymmetric sinuses and history of bicuspid aortic valve (a fusion of right and left leaflets). The mirror plane of the non-coronary sinus is shown in blue. A corresponding schematic diagram showing an idealized representation of a similarly asymmetric sinus geometry and leaflet coaptation area is also shown in FIG. 14 for comparison.

Leaflet Materials and Construction

Leaflets can be formed from a biological material or from a synthetic material that is biocompatible, resists clotting, and has functional mechanical properties similar to native leaflets. The material comprising the leaflet can be chemically or physically treated to prevent immunological reaction, calcification, or fatigue. Exemplary biological materials can include, but are not limited to human, bovine, or porcine pericardium. Human, porcine, or bovine valve leaflets are also contemplated as materials from which new leaflets may be constructed. Biological materials used to construct leaflets may be fixed, for example, using glutaraldehyde or other fixative, or a photofixation procedure such as described in U.S. Pat. No. 5,147,514, incorporated herein by reference. Alternatively leaflets may be formed using a synthetic material such as a polymer or a woven fabric. Exemplary synthetic materials include, but are not limited to, silicone, polyurethane (PU), polycarbonate urethane, or PTFE. Other synthetic materials as described in (Claiborne, et al, *Expert Rev Med Devices*. 2012 November; 9(6): 577-594; incorporated by reference herein) may be used and include, but are not limited to, a nanocomposite polymer comprised of polyhedral oligomeric silsesquioxane nanoparticles and polycarbonate urethane, PU with a poly(dimethylsiloxane) soft segment (for example, Elast-Eon™ by AorTech Biomaterials), polytetramethylene glycol-based PU (for example, Pellethane® 2363-80AE elastomer by Lubrizol), a tri-block copolymer thermoplastic polyolefin poly(styrene-block-isobutylene-block-styrene [SIBS] (Boston Scientific); xSIBS (Innovia LLC), fluoropolymers such as polyvinylidene difluoride and poly(vinylidene fluoride-co-hexafluoropropene), hyperbranched PUs demonstrating shape memory property, and nano-organic clay-PU composites.

In some embodiments, the dimensions of the sinus-matched leaflet geometry are used to generate a template to guide cutting of a sheet of selected material, for example pericardial tissue, from which a physical leaflet is to be made. In one embodiment, the selected material is placed on a cutting surface, said surface being either planar or non-planar, and the template overlaid on the selected material. Material extending beyond the boundaries of the template is cut away using a cutting tool, such as a razor blade, to produce a leaflet comprised of the selected material. In another embodiment, the geometric data describing sinus-matched leaflet may be used to generate a curved mounting surface for use as a template, for example by 3D printing or other fabrication techniques, upon which leaflet material may be positioned and trimmed to the desired shape. In another embodiment, for example when a polymeric, synthetic, or other non-biological material is to be used to generate leaflets, the geometric data describing sinus-matched leaflet may be used to construct a mold form from which leaflets may be cast.

Leaflets designed using the methods described herein may be utilized for the surgical repair of heart valves. In some embodiments, the sinus-matched leaflets may be attached or incorporated into a frame or stent type of structure to serve as a component of a prosthetic or bioprosthetic heart valve. In embodiments, these prosthetic and bioprosthetic devices may have an axisymmetric design as is typical of heart valves known in the art or available commercially. In other embodiments, the sinus-matched leaflets may be affixed to non-axisymmetric frames or heart valve designs that better conform to the anatomy of the patient. In still further embodiments, one or more sinus-matched leaflets may be may be configured for direct surgical attachment to the wall of the aortic root. It is also contemplated that sinus-matched leaflets be constructed as individual elements for incorporation into a prosthetic or bioprosthetic heart valve or direct wall attachment, or that two leaflets or three leaflets be configured as a single unit for incorporation into a prosthetic or bioprosthetic heart valve or direct wall attachment. Exemplary approaches for incorporating sinus-matched leaflets into a frame, stent, prosthesis, or bioprosthesis, or for direct attachment of sinus-matched leaflets to an aortic root include, but are not limited to, devices and methods described in U.S. Pat. Nos. 6,338,740, 6,585,766, 7,179,290, 5,156,621, US Patent Application Publication US 2009/012477 A1, and US Patent Application Publication US 2016/0000560.

Study of Predicted Valve Geometry and Coaptation Areas

A study was performed to compare the leaflet geometries generated using the disclosed sinus-matching methodology for a population of patients having normal tricuspid aortic valves (TAV) versus a population having bicuspid aortic valve (BAV). The aim of the study was to first characterize the normal range of coaptation area for a TAV population having normal sinus geometry (the "control" group) when leaflet geometries were generated (i.e., predicted) using the disclosed sinus-matching methodology; and then to compare the coaptation areas for a BAV population having a higher degree of sinus asymmetry (the "case" group) when leaflets were generated using the same methodology. It was hypothesized that sinus-matched trileaflet valves predicted from both populations would be structurally identical as defined by total valve coaptation areas, centroid line length, and centroid orientation.

Methods: Subjects with normal annulus diameters had either TAV and no stenosis/regurgitation (n=50) or BAV and varying degrees of stenosis and insufficiency (n=50). Sinus-matched valves were created using a commercially available computer-aided design software (Mimics Innovation Suite v17.0, Materialise, Belgium). All subjects had cardiac MR angiography. Blinded DICOM data was exported for segmentation, and wrapping and hollowing operations performed to isolate the 3D contour of the aortic sinuses comprising the aortic root (FIG. 5A). Three mirror planes were created from the ceiling points (commissure points) and base points (nadir points) associated with each sinus (FIG. 5B). Each of the sinuses served as a template for its corresponding leaflet (FIG. 5C) and the templates were mirrored across the mirror planes in order to produce sinus-matched valve leaflet geometries that intersected each other within the aortic root boundary (FIG. 5D). Individual coaptation areas between adjacent leaflet pairs and the total coaptation of the trileaflet set were determined using the methods described herein and the length and orientation of the Centroid Line were calculated. In addition, the area of the annulus at proximal and the body surface area were measured and used to normalize data for statistical comparisons.

Results: All but two individuals were found to have three identifiable sinuses in the aortic root. Among the BAV subjects in the case population, almost all had RL (right-left) commissural fusion. There was no difference in annulus area defined as the opening formed by a plane that includes the nadir points 123 between the case and control populations when adjusted by body surface area.

Figure 7:
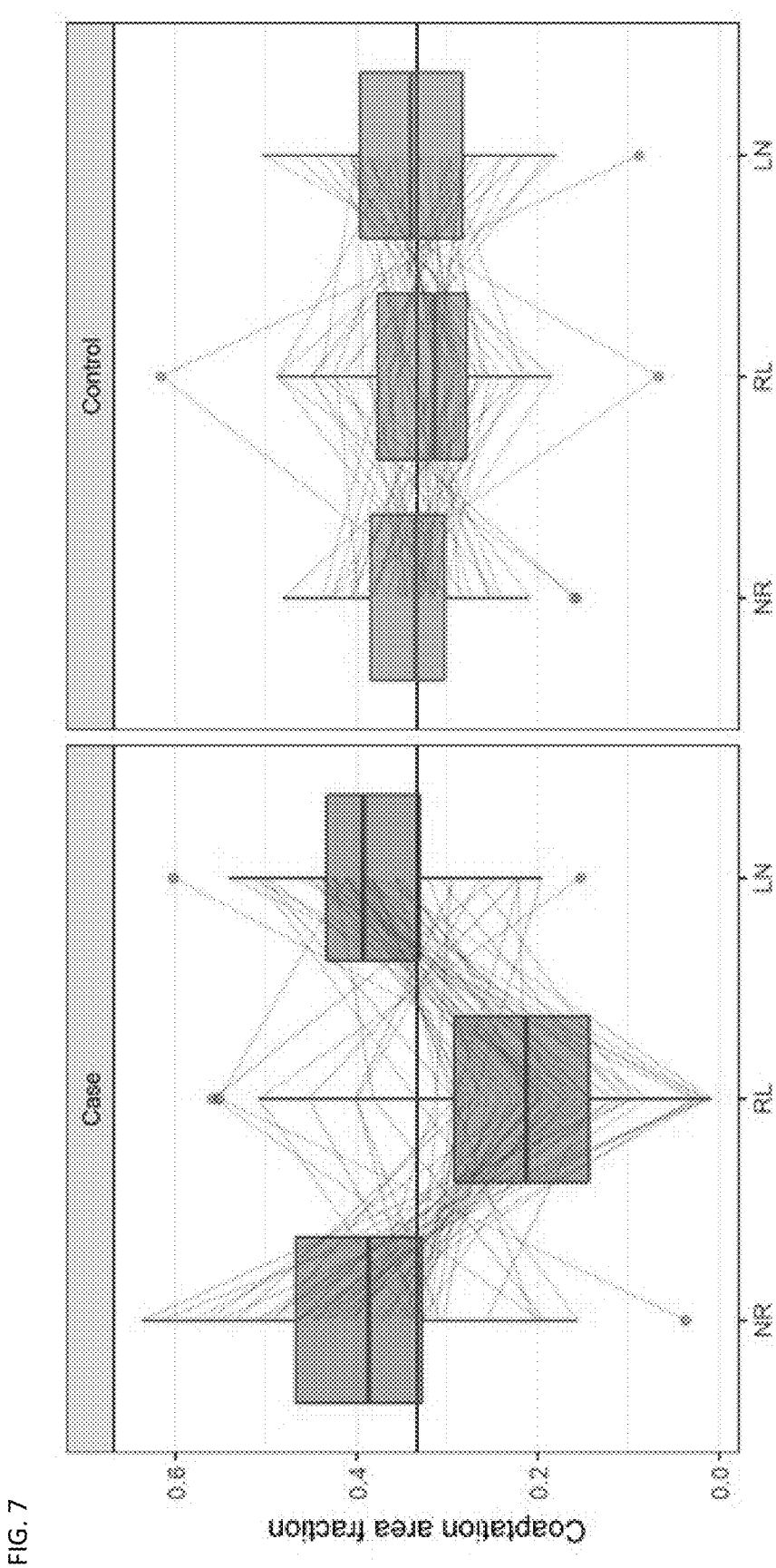
FIG. 7 is set of two graphs showing coaptation area fractions (individual leaflet coaptation area/total valve coaptation area) for a case population and a control population.

FIG. 7 shows a comparison of coaptation area fractions (individual coaptation area/total coaptation area) between the right and left coronary sinus leaflets (RL), the left and non-coronary sinus leaflets (LN), and the non- and right coronary sinus leaflets (NR) for the case and control populations. As shown, in the control population the individual leaflet coaptation area values were similar, reflecting the relative symmetry of the sinus and sinus-matched leaflets. In the case population, however, the RL coaptation area fraction was less than the NR and LN case area fractions, and significantly less than corresponding RL controls (p<0.001). Thus, there were marked asymmetries in individual sinus morphologies between cases and controls (see for example, the difference in the predicted valve leaflet shapes and coaptation in FIG. 10A).

Figure 8:
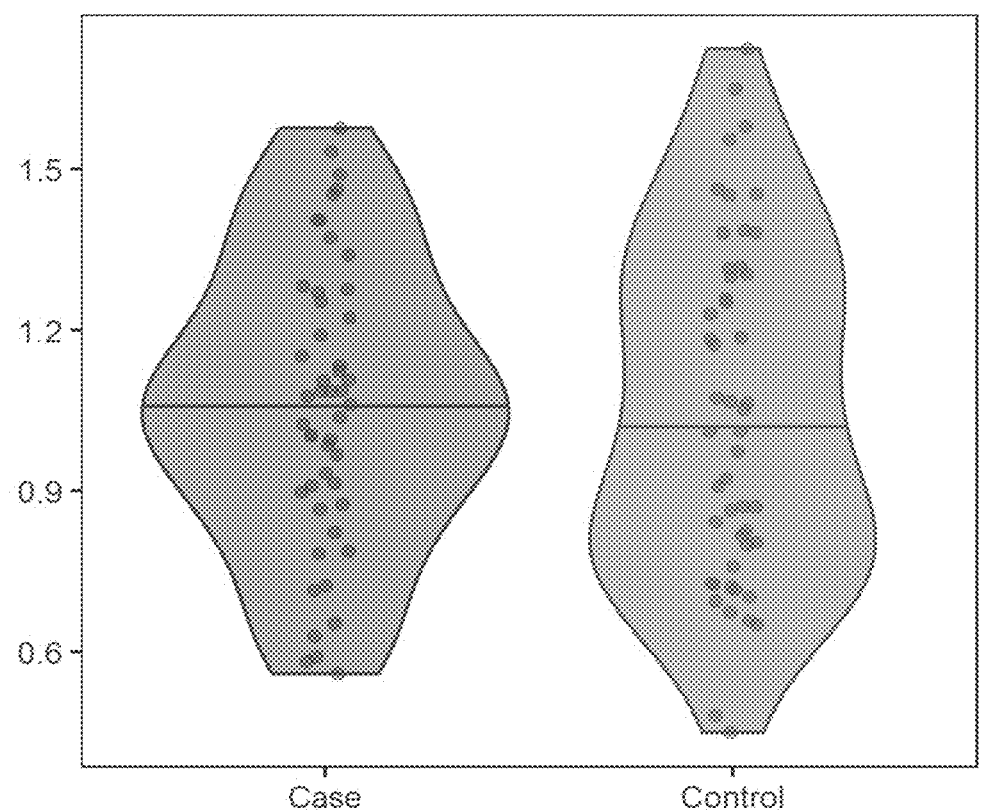
FIG. 8 is a plot of total valve coaptation area indexed to proximal annulus area for case and control populations.

FIG. 8 shows a comparison the total coaptation area for case and control populations, with the total coaptation area adjusted by annulus area. As shown, there was no difference in annulus-adjusted total coaptation areas of predicted valves when comparing cases and controls (1.07+/−0.3 SD versus 1.05+/−0.3 SD, p=0.88).

Figure 9:
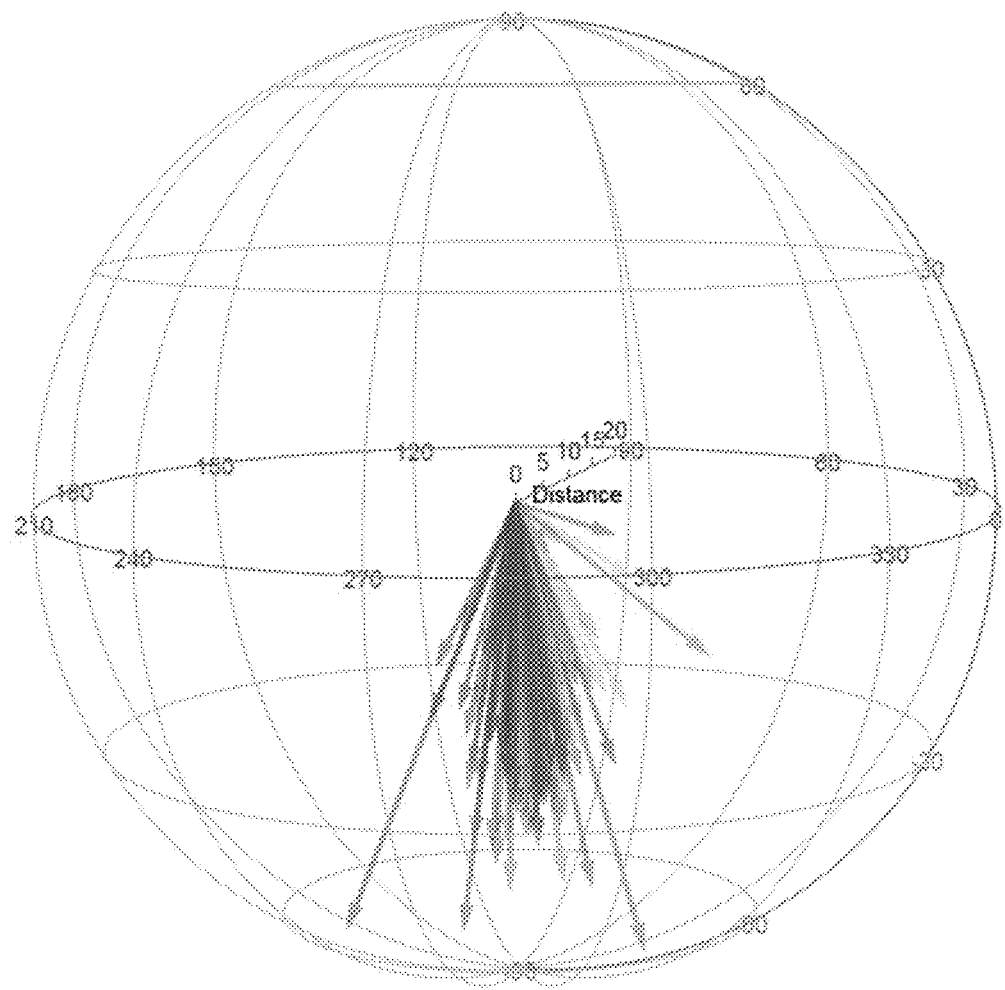
FIG. 9 is a 3D plot of length and orientation of Centroid Line for case (red) and control (blue) subjects.

FIG. 9 shows a 3D representation of Centroid Line length an orientation for case (red) and control (blue) subjects where the lines have been translated to a common origin. Orientation was not found to be statistically different between the two populations (p=0.17), but Centroid Line length was less in cases as compared with controls (p=0.006).

Summary: Previously gathered data showing that aortic root diameter and severity of aortic stenosis appear to unrelated (see FIG. 2) suggests that using aortic sinus shape as a template to predict the shape of a healthy aortic valve is a reasonable approach. The present study using TAV (controls) and BAV (cases) subjects compares the predicted valve structures that are generated using the methods disclosed herein. Centroid Line length is shorter in valves predicted from subjects with BAV (cases) than from subjects with TAV (controls) morphology, but Centroid Line orientation is similar.

Figure 10A:
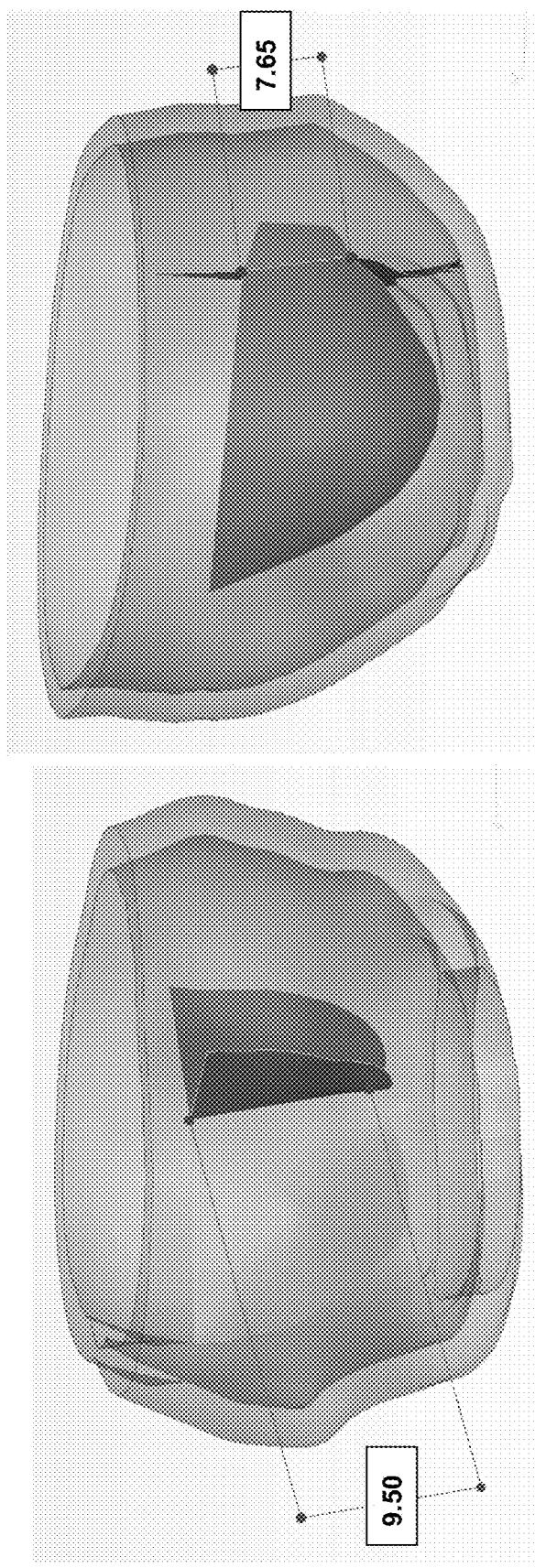
FIG. 10A shows reconstructions from two subjects representative of control (left) and case (right) sinus-mirrored valves.

BAV subjects with right-left commissural fusion typically have three sinuses. However, the predicted coaptation areas of RL leaflet is significantly smaller than either the LN or NR leaflet coaptation areas which is to be expected when valve leaflets are generated from asymmetric sinuses. However, when total coaptation area is considered, comparison of sinus-matched aortic valve morphology between TAV and BAV subjects shows that the total coaptation areas are similar (i.e., not significantly different). FIG. 10A shows an example of a representative control and case prediction generated as a part of this study. These sinus reconstructions and predicted valves highlight the marked asymmetry in the case's sinus morphology and hence in the sinus-matched leaflet coaptation areas.

Together, these data in combination with the methods disclosed in this application provide the normal range of total coaptation area for valves predicted from humans with symmetrical aortic sinuses and creates a method for clinicians to have confidence that the coaptation area of a patient-specific sinus-matched prosthesis could be competent by comparing the predicted total coaptation area to an established normal value. Thus, it is possible to measure the total coaptation area in a patient with a sinus-mirrored valve and compare that value with the mean value of predicted valves derived from a normal population. If the patient's coaptation area is within a prescribed threshold of the normal population, for example, one standard deviation (or 1.5 or 2 SD in other embodiments), it could be deemed likely to be a competent valve and potentially a suitable valve for implantation. For example, in FIG. 13 a case of a patient with a bicuspid valve is shown where a sinus-mirrored valve in the closed (diastolic) position is generated. Using the method described herein the annulus-adjusted total coaptation area is determined to be 0.78 cm/annulus area. Since the mean+/−SD of the normal population was found to be 1.05+/−0.3 this patient's annulus-adjusted coaptation area is within 1 SD of the normal population mean value and thus deemed potentially suitable for implantation.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A stentless aortic valve prosthesis tailored to the native sinus anatomy of a subject's aortic root prepared by the steps of:

receiving a three-dimensional anatomical imaging data set spanning and corresponding to at least a portion of the patient-specific geometry of the aortic root of the subject;

segmenting from the three-dimensional anatomical imaging data set a geometric surface data set that includes an inner aortic root surface and three aortic sinus surfaces;

identifying a first, second, and third ceiling point on the inner aortic root surface of the geometric surface data set;

truncating the geometric surface data set at the level of a plane passing through the first, second, and third ceiling points, thereby generating a truncated geometric surface data set;

for each of the three aortic sinus surfaces within the truncated geometric surface data set:
identifying two of the ceiling points and a base point for the aortic sinus surface;
calculating a construction plane passing through the two ceiling points and the base point of the truncated geometric surface data set;

calculating an intersection of the construction plane and the truncated geometric surface data set to define a concave leaflet surface;

extracting from the concave leaflet surface a leaflet wall curve where the concave leaflet surface is in contact with the construction plane;

constructing an anchoring flange surface based on the leaflet wall curves from each of the three aortic sinus surfaces from the truncated geometric surface data set; and joining the three concave leaflet surfaces with the anchoring flange to form a stentless aortic valve prosthesis.

2. The stentless aortic valve prosthesis of claim 1, wherein the inner aortic root surface of the geometric surface data set includes a proximal end and a distal end, and further comprising an anatomically shaped suture ring affixed to the anchoring flange, wherein the shape of the suture ring is defined by the intersection of a plane with the inner aortic root surface of the geometric surface data set at a specified distance between the proximal end and the distal end.

3. The aortic valve prosthesis of any of claims 1 and 2 wherein the aortic valve leaflet is a bioprosthetic aortic valve leaflet.

4. The aortic valve prosthesis of claim 3 wherein the bioprosthetic aortic valve leaflet comprises porcine tissue.

5. The aortic valve prosthesis of claim 3 wherein the bioprosthetic aortic valve leaflet comprises bovine tissue.

6. The aortic valve prosthesis of claim 3 wherein the bioprosthetic aortic valve leaflet comprises human tissue.

7. The aortic valve prosthesis of any of claims 1 and 2 wherein the aortic valve leaflet comprises a synthetic material.

8. The aortic valve prosthesis of claim 7 wherein the synthetic material is selected from the group of a polymer or woven fabric.

9. The aortic valve prosthesis of claim 7 wherein the synthetic material is selected from the group of silicone, polyurethane, polycarbonate urethane, and polytetrafluoroethylene.

10. The stentless aortic valve prosthesis of claim 1, wherein the anchoring flange has a width of from 0.5 mm to 8 mm.

* * * * *